United States Patent [19]
Rueger et al.

[11] Patent Number: 5,344,654
[45] Date of Patent: Sep. 6, 1994

[54] PROSTHETIC DEVICES HAVING ENHANCED OSTEOGENIC PROPERTIES

[75] Inventors: David C. Rueger, Hopkinton; Thangavel Kuberasampath; Hermann Oppermann, both of Medway; Engin Ozkaynak, Milford, all of Mass.

[73] Assignee: Stryker Corporation, Kalamazoo, Mich.

[21] Appl. No.: 901,703

[22] Filed: Jun. 16, 1992

Related U.S. Application Data

[60] Continuation-in-part of Ser. No. 841,646, Feb. 21, 1992, Pat. No. 5,266,683, which is a continuation-in-part of Ser. No. 827,052, Jan. 28, 1992, Pat. No. 5,250,302, Ser. No. 579,865, Sep. 7, 1990, Pat. No. 5,108,753, Ser. No. 621,849, Dec. 4, 1990, abandoned, Ser. No. 621,988, Dec. 4, 1990, abandoned, Ser. No. 810,560, Dec. 20, 1991, abandoned, Ser. No. 569,920, Aug. 20, 1990, abandoned, Ser. No. 600,024, Oct. 18, 1990, abandoned, Ser. No. 599,543, Oct. 18, 1990, abandoned, Ser. No. 616,374, Nov. 21, 1990, Pat. No. 5,162,114, and Ser. No. 483,913, Feb. 22, 1990, Pat. No. 5,171,574, said Ser. No. 827,052, is a division of Ser. No. 179,406, Apr. 8, 1988, Pat. No. 4,968,590, said Ser. No. 579,865, is a division of Ser. No. 179,406, Apr. 8, 1988, said Ser. No. 621,849, is a division of Ser. No. 232,630, Aug. 15, 1988, abandoned, which is a continuation-in-part of Ser. No. 179,406, Apr. 8, 1988, said Ser. No. 621,988, is a division of Ser. No. 315,342, Feb. 23, 1989, Pat. No. 5,011,691, which is a continuation-in-part of Ser. No. 232,630, Aug. 15, 1988, said Ser. No. 810,560, is a continuation of Ser. No. 660,162, Feb. 22, 1991, abandoned, which is a continuation of Ser. No. 422,699, Oct. 17, 1989, abandoned, which is a continuation-in-part of Ser. No. 315,342, Feb. 23, 1989, said Ser. No. 569,920, is a continuation-in-part of Ser. No. 422,613, Oct. 19, 1989, and Ser. No. 483,913, Feb. 22, 1990, which is a continuation-in-part of Ser. No. 422,613, Oct. 17, 1989, Pat. No. 4,975,526, which is a continuation-in-part of Ser. No. 315,342, Feb. 23, 1989, said Ser. No. 600,024, is a continuation-in-part of Ser. No. 569,920, Aug. 20, 1990, said Ser. No. 599,543.

[51] Int. Cl.$^5$ .................... A61L 27/00; A61F 2/30; A61K 35/32

[52] U.S. Cl. .................... 424/423; 424/426; 523/105; 523/115; 525/937; 604/891.1

[58] Field of Search .............. 424/423, 426; 514/2, 514/21; 523/105, 115; 525/937; 604/891.1

[56] References Cited

U.S. PATENT DOCUMENTS

| 4,394,370 | 7/1983 | Jefferies | 350/353 |
|---|---|---|---|
| 4,563,350 | 1/1986 | Nathan et al. | 424/95 |
| 4,563,489 | 1/1986 | Urist | 424/426 |
| 4,596,574 | 6/1986 | Urist | 424/426 |
| 4,968,590 | 11/1990 | Kuberasampath et al. | 424/426 |
| 5,011,691 | 4/1991 | Oppermann et al. | 424/426 |
| 5,108,436 | 4/1992 | Chu et al. | 623/16 |
| 5,207,710 | 5/1993 | Chu et al. | 623/16 |

FOREIGN PATENT DOCUMENTS

| 0106946 | 7/1983 | European Pat. Off. |
| 0169001 | 7/1985 | European Pat. Off. |
| 0182483 | 5/1986 | European Pat. Off. |
| 0361896 | 4/1990 | European Pat. Off. |
| 0413492 | 2/1991 | European Pat. Off. |
| 0470305 | 2/1992 | European Pat. Off. |
| 2534593 | 2/1975 | Fed. Rep. of Germany. |
| WO8600526 | 1/1986 | PCT Int'l Appl. |
| WO88/00205 | 1/1988 | PCT Int'l Appl. |
| WO91/05802 | 5/1991 | PCT Int'l Appl. |

OTHER PUBLICATIONS

Collagen Res. Res. vol. 7 (1987), pp. 225–231.
The Journal of Arthroplasty vol. 2 (1987) 163–176.
Cook et al., Clin. Orth. & Rel. Res. 232 (1988) 225–243.
Lynch et al., J. Periodontol 62 (1991) 710–716.
Reddi et al., J. Biom. Mat. Res. 19 (1985) 233–239.

Primary Examiner—Nathan M. Nutter
Attorney, Agent, or Firm—Testa, Hurwitz & Thibeault

[57] ABSTRACT

A prosthetic device comprising a prosthesis coated with substantially pure osteogenic protein is disclosed. A method for biologically fixing prosthetic devices in vivo is also disclosed. In this method, a prosthesis is implanted in an individual in contact with a substantially pure osteogenic protein, enhancing the strength of the bond between the prosthesis and the existing bone at the joining site.

33 Claims, 1 Drawing Sheet

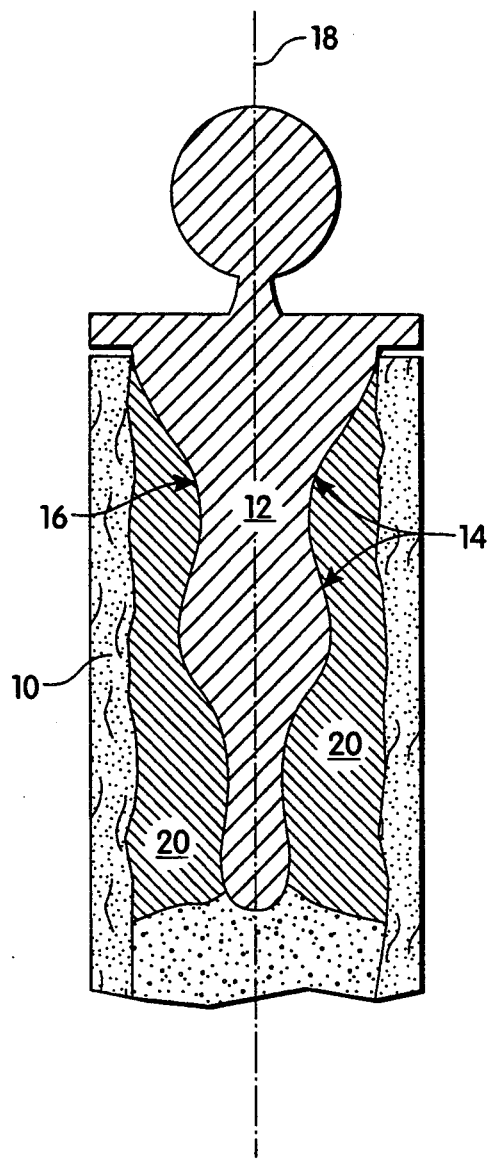

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 1822 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: HOMO SAPIENS
        ( F ) TISSUE TYPE: HIPPOCAMPUS ( i x ) FEATURE:
        ( A ) NAME/KEY: CDS
        ( B ) LOCATION: 49..1341
        ( C ) IDENTIFICATION METHOD: experimental
        ( D ) OTHER INFORMATION: /function="OSTEOGENIC PROTEIN"
            / product="OP1"
            / evidence=EXPERIMENTAL
            / standardname="OP1"

( x i ) SEQUENCE DESCRIPTION: SEQ ID NO:1:

```
GGTGCGGGCC CGGAGCCCGG AGCCCGGGTA GCGCGTAGAG CCGGCGCG ATG CAC GTG              57
                                                     Met His Val
                                                      1

CGC TCA CTG CGA GCT GCG GCG CCG CAC AGC TTC GTG GCG CTC TGG GCA             105
Arg Ser Leu Arg Ala Ala Ala Pro His Ser Phe Val Ala Leu Trp Ala
     5              10                  15

CCC CTG TTC CTG CTG CGC TCC GCC CTG GCC GAC TTC AGC CTG GAC AAC             153
Pro Leu Phe Leu Leu Arg Ser Ala Leu Ala Asp Phe Ser Leu Asp Asn
 20              25                  30                      35

GAG GTG CAC TCG AGC TTC ATC CAC CGG CGC CTC CGC AGC CAG GAG CGG             201
Glu Val His Ser Ser Phe Ile His Arg Arg Leu Arg Ser Gln Glu Arg
             40                  45                  50

CGG GAG ATG CAG CGC GAG ATC CTC TCC ATT TTG GGC TTG CCC CAC CGC             249
Arg Glu Met Gln Arg Glu Ile Leu Ser Ile Leu Gly Leu Pro His Arg
             55                  60                  65

CCG CGC CCG CAC CTC CAG GGC AAG CAC AAC TCG GCA CCC ATG TTC ATG             297
Pro Arg Pro His Leu Gln Gly Lys His Asn Ser Ala Pro Met Phe Met
         70                  75                  80

CTG GAC CTG TAC AAC GCC ATG GCG GTG GAG GAG GGC GGG GGG CCC GGC             345
Leu Asp Leu Tyr Asn Ala Met Ala Val Glu Glu Gly Gly Gly Pro Gly
 85                  90                  95

GGC CAG GGC TTC TCC TAC CCC TAC AAG GCC GTC TTC AGT ACC CAG GGC             393
Gly Gln Gly Phe Ser Tyr Pro Tyr Lys Ala Val Phe Ser Thr Gln Gly
100     105 110     115

CCC CCT CTG GCC AGC CTG CAA GAT AGC CAT TTC CTC ACC GAC GCC GAC             441
Pro Pro Leu Ala Ser Leu Gln Asp Ser His Phe Leu Thr Asp Ala Asp
             120             125                 130

ATG GTC ATG AGC TTC GTC AAC CTC GTG GAA CAT GAC AAG GAA TTC TTC             489
Met Val Met Ser Phe Val Asn Leu Val Glu His Asp Lys Glu Phe Phe
             135                 140                 145

CAC CCA CGC TAC CAC CAT CGA GAG TTC CGG TTT GAT CTT TCC AAG ATC             537
His Pro Arg Tyr His His Arg Glu Phe Arg Phe Asp Leu Ser Lys Ile
         150             155                 160

CCA GAA GGG GAA GCT GTC ACG GCA GCC GAA TTC CGG ATC TAC AAG GAC             585
Pro Glu Gly Glu Ala Val Thr Ala Ala Glu Phe Arg Ile Tyr Lys Asp
     165                 170                 175
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| TAC | ATC | CGG | GAA | CGC | TTC | GAC | AAT | GAG | ACG | TTC | CGG | ATC | AGC | GTT | TAT | 633 |
| Tyr | Ile | Arg | Glu | Arg | Phe | Asp | Asn | Glu | Thr | Phe | Arg | Ile | Ser | Val | Tyr | |
| 180 | | | | 185 | | | | | 190 | | | | | | 195 | |
| CAG | GTG | CTC | CAG | GAG | CAC | TTG | GGC | AGG | GAA | TCG | GAT | CTC | TTC | CTG | CTC | 681 |
| Gln | Val | Leu | Gln | Glu | His | Leu | Gly | Arg | Glu | Ser | Asp | Leu | Phe | Leu | Leu | |
| | | | | 200 | | | | | 205 | | | | | 210 | | |
| GAC | AGC | CGT | ACC | CTC | TGG | GCC | TCG | GAG | GAG | GGC | TGG | CTG | GTG | TTT | GAC | 729 |
| Asp | Ser | Arg | Thr | Leu | Trp | Ala | Ser | Glu | Glu | Gly | Trp | Leu | Val | Phe | Asp | |
| | | | 215 | | | | | 220 | | | | | 225 | | | |
| ATC | ACA | GCC | ACC | AGC | AAC | CAC | TGG | GTG | GTC | AAT | CCG | CGG | CAC | AAC | CTG | 777 |
| Ile | Thr | Ala | Thr | Ser | Asn | His | Trp | Val | Val | Asn | Pro | Arg | His | Asn | Leu | |
| | | | 230 | | | | | 235 | | | | | 240 | | | |
| GGC | CTG | CAG | CTC | TCG | GTG | GAG | ACG | CTG | GAT | GGG | CAG | AGC | ATC | AAC | CCC | 825 |
| Gly | Leu | Gln | Leu | Ser | Val | Glu | Thr | Leu | Asp | Gly | Gln | Ser | Ile | Asn | Pro | |
| | | 245 | | | | | 250 | | | | | 255 | | | | |
| AAG | TTG | GCG | GGC | CTG | ATT | GGG | CGG | CAC | GGG | CCC | CAG | AAC | AAG | CAG | CCC | 873 |
| Lys | Leu | Ala | Gly | Leu | Ile | Gly | Arg | His | Gly | Pro | Gln | Asn | Lys | Gln | Pro | |
| 260 | | | | | 265 | | | | | 270 | | | | | 275 | |
| TTC | ATG | GTG | GCT | TTC | TTC | AAG | GCC | ACG | GAG | GTC | CAC | TTC | CGC | AGC | ATC | 921 |
| Phe | Met | Val | Ala | Phe | Phe | Lys | Ala | Thr | Glu | Val | His | Phe | Arg | Ser | Ile | |
| | | | | 280 | | | | | 285 | | | | | 290 | | |
| CGG | TCC | ACG | GGG | AGC | AAA | CAG | CGC | AGC | CAG | AAC | CGC | TCC | AAG | ACG | CCC | 969 |
| Arg | Ser | Thr | Gly | Ser | Lys | Gln | Arg | Ser | Gln | Asn | Arg | Ser | Lys | Thr | Pro | |
| | | | 295 | | | | | 300 | | | | | 305 | | | |
| AAG | AAC | CAG | GAA | GCC | CTG | CGG | ATG | GCC | AAC | GTG | GCA | GAG | AAC | AGC | AGC | 1017 |
| Lys | Asn | Gln | Glu | Ala | Leu | Arg | Met | Ala | Asn | Val | Ala | Glu | Asn | Ser | Ser | |
| | | 310 | | | | | 315 | | | | | 320 | | | | |
| AGC | GAC | CAG | AGG | CAG | GCC | TGT | AAG | AAG | CAC | GAG | CTG | TAT | GTC | AGC | TTC | 1065 |
| Ser | Asp | Gln | Arg | Gln | Ala | Cys | Lys | Lys | His | Glu | Leu | Tyr | Val | Ser | Phe | |
| | 325 | | | | | 330 | | | | | 335 | | | | | |
| CGA | GAC | CTG | GGC | TGG | CAG | GAC | TGG | ATC | ATC | GCG | CCT | GAA | GGC | TAC | GCC | 1113 |
| Arg | Asp | Leu | Gly | Trp | Gln | Asp | Trp | Ile | Ile | Ala | Pro | Glu | Gly | Tyr | Ala | |
| 340 | | | | | 345 | | | | | 350 | | | | | 355 | |
| GCC | TAC | TAC | TGT | GAG | GGG | GAG | TGT | GCC | TTC | CCT | CTG | AAC | TCC | TAC | ATG | 1161 |
| Ala | Tyr | Tyr | Cys | Glu | Gly | Glu | Cys | Ala | Phe | Pro | Leu | Asn | Ser | Tyr | Met | |
| | | | | 360 | | | | | 365 | | | | | 370 | | |
| AAC | GCC | ACC | AAC | CAC | GCC | ATC | GTG | CAG | ACG | CTG | GTC | CAC | TTC | ATC | AAC | 1209 |
| Asn | Ala | Thr | Asn | His | Ala | Ile | Val | Gln | Thr | Leu | Val | His | Phe | Ile | Asn | |
| | | | 375 | | | | | 380 | | | | | 385 | | | |
| CCG | GAA | ACG | GTG | CCC | AAG | CCC | TGC | TGT | GCG | CCC | ACG | CAG | CTC | AAT | GCC | 1257 |
| Pro | Glu | Thr | Val | Pro | Lys | Pro | Cys | Cys | Ala | Pro | Thr | Gln | Leu | Asn | Ala | |
| | | 390 | | | | | 395 | | | | | 400 | | | | |
| ATC | TCC | GTC | CTC | TAC | TTC | GAT | GAC | AGC | TCC | AAC | GTC | ATC | CTG | AAG | AAA | 1305 |
| Ile | Ser | Val | Leu | Tyr | Phe | Asp | Asp | Ser | Ser | Asn | Val | Ile | Leu | Lys | Lys | |
| | 405 | | | | | 410 | | | | | 415 | | | | | |
| TAC | AGA | AAC | ATG | GTG | GTC | CGG | GCC | TGT | GGC | TGC | CAC | TAGCTCCTCC | | | 1351 | |
| Tyr | Arg | Asn | Met | Val | Val | Arg | Ala | Cys | Gly | Cys | His | | | | | |
| 420 | | | | 425 | | | | | 430 | | | | | | | |

| | | | | | |
| --- | --- | --- | --- | --- | --- |
| GAGAATTCAG | ACCCTTTGGG | GCCAAGTTTT | TCTGGATCCT | CCATTGCTCG | CCTTGGCCAG | 1411 |
| GAACCAGCAG | ACCAACTGCC | TTTTGTGAGA | CCTTCCCCTC | CCTATCCCCA | ACTTTAAAGG | 1471 |
| TGTGAGAGTA | TTAGGAAACA | TGAGCAGCAT | ATGGCTTTTG | ATCAGTTTTT | CAGTGGCAGC | 1531 |
| ATCCAATGAA | CAAGATCCTA | CAAGCTGTGC | AGGCAAAACC | TAGCAGGAAA | AAAAAACAAC | 1591 |
| GCATAAAGAA | AAATGGCCGG | GCCAGGTCAT | TGGCTGGGAA | GTCTCAGCCA | TGCACGGACT | 1651 |
| CGTTTCCAGA | GGTAATTATG | AGCGCCTACC | AGCCAGGCCA | CCCAGCCGTG | GGAGGAAGGG | 1711 |
| GGCGTGGCAA | GGGGTGGGCA | CATTGGTGTC | TGTGCGAAAG | GAAAATTGAC | CCGGAAGTTC | 1771 |
| CTGTAATAAA | TGTCACAATA | AAACGAATGA | ATGAAAAAAA | AAAAAAAAA | A | 1822 |

(2) INFORMATION FOR SEQ ID NO:2:

(i) SEQUENCE CHARACTERISTICS:
        (A) LENGTH: 431 amino acids
        (B) TYPE: amino acid
        (D) TOPOLOGY: linear (ii) MOLECULE TYPE: protein (xi) SEQUENCE DESCRIPTION: SEQ ID NO:2:

```
Met His Val Arg Ser Leu Arg Ala Ala Ala Pro His Ser Phe Val Ala
 1               5                  10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
 50                  55                  60

Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
370                 375                 380
```

```
Phe  Ile  Asn  Pro  Glu  Thr  Val  Pro  Lys  Pro  Cys  Ala  Pro  Thr  Gln
385                 390                 395                      400

Leu  Asn  Ala  Ile  Ser  Val  Leu  Tyr  Phe  Asp  Asp  Ser  Ser  Asn  Val  Ile
               405                      410                      415

Leu  Lys  Lys  Tyr  Arg  Asn  Met  Val  Val  Arg  Ala  Cys  Gly  Cys  His
          420                      425                      430
```

(2) INFORMATION FOR SEQ ID NO:3:

(i) SEQUENCE CHARACTERISTICS:
    (A) LENGTH: 96 amino acids
    (B) TYPE: amino acid
    (C) STRANDEDNESS: single
    (D) TOPOLOGY: linear (ii) MOLECULE TYPE: protein (ix) FEATURE:
    (A) NAME/KEY: Protein
    (B) LOCATION: 1..96
    (D) OTHER INFORMATION: /note="COP-5"

(xi) SEQUENCE DESCRIPTION: SEQ ID NO:3:

```
Leu  Tyr  Val  Asp  Phe  Ser  Asp  Val  Gly  Trp  Asp  Asp  Trp  Ile  Val  Ala
1                   5                   10                      15

Pro  Pro  Gly  Tyr  Gln  Ala  Phe  Tyr  Cys  His  Gly  Glu  Cys  Pro  Phe  Pro
               20                  25                           30

Leu  Ala  Asp  His  Phe  Asn  Ser  Thr  Asn  His  Ala  Val  Val  Gln  Thr  Leu
          35                  40                       45

Val  Asn  Ser  Val  Asn  Ser  Lys  Ile  Pro  Lys  Ala  Cys  Cys  Val  Pro  Thr
     50                  55                       60

Glu  Leu  Ser  Ala  Ile  Ser  Met  Leu  Tyr  Leu  Asp  Glu  Asn  Glu  Lys  Val
65                  70                       75                      80

Val  Leu  Lys  Asn  Tyr  Gln  Glu  Met  Val  Val  Glu  Gly  Cys  Gly  Cys  Arg
               85                  90                       95
```

(2) INFORMATION FOR SEQ ID NO:4:

(i) SEQUENCE CHARACTERISTICS:
    (A) LENGTH: 96 amino acids
    (B) TYPE: amino acid
    (C) STRANDEDNESS: single
    (D) TOPOLOGY: linear (ii) MOLECULE TYPE: protein (ix) FEATURE:
    (A) NAME/KEY: Protein
    (B) LOCATION: 1..96
    (D) OTHER INFORMATION: /note="COP-7"

(xi) SEQUENCE DESCRIPTION: SEQ ID NO:4:

```
Leu  Tyr  Val  Asp  Phe  Ser  Asp  Val  Gly  Trp  Asn  Asp  Trp  Ile  Val  Ala
1                   5                   10                      15

Pro  Pro  Gly  Tyr  His  Ala  Phe  Tyr  Cys  His  Gly  Glu  Cys  Pro  Phe  Pro
               20                  25                           30

Leu  Ala  Asp  His  Leu  Asn  Ser  Thr  Asn  His  Ala  Val  Val  Gln  Thr  Leu
          35                  40                       45

Val  Asn  Ser  Val  Asn  Ser  Lys  Ile  Pro  Lys  Ala  Cys  Cys  Val  Pro  Thr
     50                  55                       60

Glu  Leu  Ser  Ala  Ile  Ser  Met  Leu  Tyr  Leu  Asp  Glu  Asn  Glu  Lys  Val
65                  70                       75                      80

Val  Leu  Lys  Asn  Tyr  Gln  Glu  Met  Val  Val  Glu  Gly  Cys  Gly  Cys  Arg
               85                  90                       95
```

( 2 ) INFORMATION FOR SEQ ID NO:5:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: DROSOPHILA MELANOGASTER ( i x ) FEATURE:
        ( A ) NAME/KEY: Protein
        ( B ) LOCATION: 1..101
        ( D ) OTHER INFORMATION: /label=DPP-FX ( x i ) SEQUENCE DESCRIPTION: SEQ ID NO:5:

```
Cys Arg Arg His Ser Leu Tyr Val Asp Phe Ser Asp Val Gly Trp Asp
1               5                   10                  15

Asp Trp Ile Val Ala Pro Leu Gly Tyr Asp Ala Tyr Tyr Cys His Gly
                20                  25                  30

Lys Cys Pro Phe Pro Leu Ala Asp His Phe Asn Ser Thr Asn His Ala
            35                  40                  45

Val Val Gln Thr Leu Val Asn Asn Asn Pro Gly Lys Val Pro Lys
        50                  55                  60

Ala Cys Cys Val Pro Thr Gln Leu Asp Ser Val Ala Met Leu Tyr Leu
65                  70                  75                  80

Asn Asp Gln Ser Thr Val Val Leu Lys Asn Tyr Gln Glu Met Thr Val
                85                  90                  95

Val Gly Cys Gly Cys Arg
            100
```

( 2 ) INFORMATION FOR SEQ ID NO:6:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: XENOPUS ( i x ) FEATURE:
        ( A ) NAME/KEY: Protein
        ( B ) LOCATION: 1..102
        ( D ) OTHER INFORMATION: /label=VG1-FX ( x i ) SEQUENCE DESCRIPTION: SEQ ID NO:6:

```
Cys Lys Lys Arg His Leu Tyr Val Glu Phe Lys Asp Val Gly Trp Gln
1               5                   10                  15

Asn Trp Val Ile Ala Pro Gln Gly Tyr Met Ala Asn Tyr Cys Tyr Gly
                20                  25                  30

Glu Cys Pro Tyr Pro Leu Thr Glu Ile Leu Asn Gly Ser Asn His Ala
            35                  40                  45

Ile Leu Gln Thr Leu Val His Ser Ile Glu Pro Glu Asp Ile Pro Leu
        50                  55                  60

Pro Cys Cys Val Pro Thr Lys Met Ser Pro Ile Ser Met Leu Phe Tyr
65                  70                  75                  80

Asp Asn Asn Asp Asn Val Val Leu Arg His Tyr Glu Asn Met Ala Val
                85                  90                  95

Asp Glu Cys Gly Cys Arg
```

100

(2) INFORMATION FOR SEQ ID NO:7:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: MURIDAE (ix) FEATURE:
        (A) NAME/KEY: Protein
        (B) LOCATION: 1..102
        (D) OTHER INFORMATION: /label=VGR-1-FX (xi) SEQUENCE DESCRIPTION: SEQ ID NO:7:

```
Cys Lys Lys His Gly Leu Tyr Val Ser Phe Gln Asp Val Gly Trp Gln
 1               5                  10                  15

Asp Trp Ile Ile Ala Pro Xaa Gly Tyr Ala Ala Asn Tyr Cys Asp Gly
            20                  25                  30

Glu Cys Ser Phe Pro Leu Asn Ala His Met Asn Ala Thr Asn His Ala
        35                  40                  45

Ile Val Gln Thr Leu Val His Val Met Asn Pro Glu Tyr Val Pro Lys
    50                  55                  60

Pro Cys Cys Ala Pro Thr Lys Val Asn Ala Ile Ser Val Leu Tyr Phe
65                  70                  75                  80

Asp Asp Asn Ser Asn Val Ile Leu Lys Lys Tyr Arg Asn Met Val Val
                85                  90                  95

Arg Ala Cys Gly Cys His
                100
```

(2) INFORMATION FOR SEQ ID NO:8:

(i) SEQUENCE CHARACTERISTICS:
        (A) LENGTH: 1873 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: MURIDAE
        (F) TISSUE TYPE: EMBRYO (ix) FEATURE:
        (A) NAME/KEY: CDS
        (B) LOCATION: 104..1393
        (D) OTHER INFORMATION: /function="OSTEOGENIC PROTEIN"
            / product="MOP1"
            / note="MOP1 (CDNA)"

(xi) SEQUENCE DESCRIPTION: SEQ ID NO:8:

```
CTGCAGCAAG TGACCTCGGG TCGTGGACCG CTGCCCTGCC CCCTCCGCTG CCACCTGGGG         60

CGGCGCGGGC CCGGTGCCCC GGATCGCGCG TAGAGCCGGC GCG ATG CAC GTG CGC        115
                                             Met His Val Arg
                                              1

TCG CTG CGC GCT GCG GCG CCA CAC AGC TTC GTG GCG CTC TGG GCG CCT        163
Ser Leu Arg Ala Ala Ala Pro His Ser Phe Val Ala Leu Trp Ala Pro
 5               10                  15                  20
```

| | | | | | | | | | | | | | | | | |
|---|---|---|---|---|---|---|---|---|---|---|---|---|---|---|---|---|
| CTG | TTC | TTG | CTG | CGC | TCC | GCC | CTG | GCC | GAT | TTC | AGC | CTG | GAC | AAC | GAG | 211 |
| Leu | Phe | Leu | Leu | Arg | Ser | Ala | Leu | Ala | Asp | Phe | Ser | Leu | Asp | Asn | Glu | |
| | | | 25 | | | | | 30 | | | | | 35 | | | |
| GTG | CAC | TCC | AGC | TTC | ATC | CAC | CGG | CGC | CTC | CGC | AGC | CAG | GAG | CGG | CGG | 259 |
| Val | His | Ser | Ser | Phe | Ile | His | Arg | Arg | Leu | Arg | Ser | Gln | Glu | Arg | Arg | |
| | | | 40 | | | | | 45 | | | | | 50 | | | |
| GAG | ATG | CAG | CGG | GAG | ATC | CTG | TCC | ATC | TTA | GGG | TTG | CCC | CAT | CGC | CCG | 307 |
| Glu | Met | Gln | Arg | Glu | Ile | Leu | Ser | Ile | Leu | Gly | Leu | Pro | His | Arg | Pro | |
| | | 55 | | | | | 60 | | | | | 65 | | | | |
| CGC | CCG | CAC | CTC | CAG | GGA | AAG | CAT | AAT | TCG | GCG | CCC | ATG | TTC | ATG | TTG | 355 |
| Arg | Pro | His | Leu | Gln | Gly | Lys | His | Asn | Ser | Ala | Pro | Met | Phe | Met | Leu | |
| | 70 | | | | | 75 | | | | | 80 | | | | | |
| GAC | CTG | TAC | AAC | GCC | ATG | GCG | GTG | GAG | GAG | AGC | GGG | CCG | GAC | GGA | CAG | 403 |
| Asp | Leu | Tyr | Asn | Ala | Met | Ala | Val | Glu | Glu | Ser | Gly | Pro | Asp | Gly | Gln | |
| 85 | | | | | 90 | | | | | 95 | | | | | 100 | |
| GGC | TTC | TCC | TAC | CCC | TAC | AAG | GCC | GTC | TTC | AGT | ACC | CAG | GGC | CCC | CCT | 451 |
| Gly | Phe | Ser | Tyr | Pro | Tyr | Lys | Ala | Val | Phe | Ser | Thr | Gln | Gly | Pro | Pro | |
| | | | | 105 | | | | | 110 | | | | | 115 | | |
| TTA | GCC | AGC | CTG | CAG | GAC | AGC | CAT | TTC | CTC | ACT | GAC | GCC | GAC | ATG | GTC | 499 |
| Leu | Ala | Ser | Leu | Gln | Asp | Ser | His | Phe | Leu | Thr | Asp | Ala | Asp | Met | Val | |
| | | | 120 | | | | | 125 | | | | | 130 | | | |
| ATG | AGC | TTC | GTC | AAC | CTA | GTG | GAA | CAT | GAC | AAA | GAA | TTC | TTC | CAC | CCT | 547 |
| Met | Ser | Phe | Val | Asn | Leu | Val | Glu | His | Asp | Lys | Glu | Phe | Phe | His | Pro | |
| | | | 135 | | | | | 140 | | | | | 145 | | | |
| CGA | TAC | CAC | CAT | CGG | GAG | TTC | CGG | TTT | GAT | CTT | TCC | AAG | ATC | CCC | GAG | 595 |
| Arg | Tyr | His | His | Arg | Glu | Phe | Arg | Phe | Asp | Leu | Ser | Lys | Ile | Pro | Glu | |
| | 150 | | | | | 155 | | | | | 160 | | | | | |
| GGC | GAA | CGG | GTG | ACC | GCA | GCC | GAA | TTC | AGG | ATC | TAT | AAG | GAC | TAC | ATC | 643 |
| Gly | Glu | Arg | Val | Thr | Ala | Ala | Glu | Phe | Arg | Ile | Tyr | Lys | Asp | Tyr | Ile | |
| 165 | | | | | 170 | | | | | 175 | | | | | 180 | |
| CGG | GAG | CGA | TTT | GAC | AAC | GAG | ACC | TTC | CAG | ATC | ACA | GTC | TAT | CAG | GTG | 691 |
| Arg | Glu | Arg | Phe | Asp | Asn | Glu | Thr | Phe | Gln | Ile | Thr | Val | Tyr | Gln | Val | |
| | | | 185 | | | | | 190 | | | | | 195 | | | |
| CTC | CAG | GAG | CAC | TCA | GGC | AGG | GAG | TCG | GAC | CTC | TTC | TTG | CTG | GAC | AGC | 739 |
| Leu | Gln | Glu | His | Ser | Gly | Arg | Glu | Ser | Asp | Leu | Phe | Leu | Leu | Asp | Ser | |
| | | | 200 | | | | | 205 | | | | | 210 | | | |
| CGC | ACC | ATC | TGG | GCT | TCT | GAG | GAG | GGC | TGG | TTG | GTG | TTT | GAT | ATC | ACA | 787 |
| Arg | Thr | Ile | Trp | Ala | Ser | Glu | Glu | Gly | Trp | Leu | Val | Phe | Asp | Ile | Thr | |
| | | 215 | | | | | 220 | | | | | 225 | | | | |
| GCC | ACC | AGC | AAC | CAC | TGG | GTG | GTC | AAC | CCT | CGG | CAC | AAC | CTG | GGC | TTA | 835 |
| Ala | Thr | Ser | Asn | His | Trp | Val | Val | Asn | Pro | Arg | His | Asn | Leu | Gly | Leu | |
| | 230 | | | | | 235 | | | | | 240 | | | | | |
| CAG | CTC | TCT | GTG | GAG | ACC | CTG | GAT | GGG | CAG | AGC | ATC | AAC | CCC | AAG | TTG | 883 |
| Gln | Leu | Ser | Val | Glu | Thr | Leu | Asp | Gly | Gln | Ser | Ile | Asn | Pro | Lys | Leu | |
| 245 | | | | | 250 | | | | | 255 | | | | | 260 | |
| GCA | GGC | CTG | ATT | GGA | CGG | CAT | GGA | CCC | CAG | AAC | AAG | CAA | CCC | TTC | ATG | 931 |
| Ala | Gly | Leu | Ile | Gly | Arg | His | Gly | Pro | Gln | Asn | Lys | Gln | Pro | Phe | Met | |
| | | | | 265 | | | | | 270 | | | | | 275 | | |
| GTG | GCC | TTC | TTC | AAG | GCC | ACG | GAA | GTC | CAT | CTC | CGT | AGT | ATC | CGG | TCC | 979 |
| Val | Ala | Phe | Phe | Lys | Ala | Thr | Glu | Val | His | Leu | Arg | Ser | Ile | Arg | Ser | |
| | | | 280 | | | | | 285 | | | | | 290 | | | |
| ACG | GGG | GGC | AAG | CAG | CGC | AGC | CAG | AAT | CGC | TCC | AAG | ACG | CCA | AAG | AAC | 1027 |
| Thr | Gly | Gly | Lys | Gln | Arg | Ser | Gln | Asn | Arg | Ser | Lys | Thr | Pro | Lys | Asn | |
| | | 295 | | | | | 300 | | | | | 305 | | | | |
| CAA | GAG | GCC | CTG | AGG | ATG | GCC | AGT | GTG | GCA | GAA | AAC | AGC | AGC | AGT | GAC | 1075 |
| Gln | Glu | Ala | Leu | Arg | Met | Ala | Ser | Val | Ala | Glu | Asn | Ser | Ser | Ser | Asp | |
| | 310 | | | | | 315 | | | | | 320 | | | | | |
| CAG | AGG | CAG | GCC | TGC | AAG | AAA | CAT | GAG | CTG | TAC | GTC | AGC | TTC | CGA | GAC | 1123 |
| Gln | Arg | Gln | Ala | Cys | Lys | Lys | His | Glu | Leu | Tyr | Val | Ser | Phe | Arg | Asp | |
| 325 | | | | 330 | | | | | 335 | | | | | 340 | | |
| CTT | GGC | TGG | CAG | GAC | TGG | ATC | ATT | GCA | CCT | GAA | GGC | TAT | GCT | GCC | TAC | 1171 |
| Leu | Gly | Trp | Gln | Asp | Trp | Ile | Ile | Ala | Pro | Glu | Gly | Tyr | Ala | Ala | Tyr | |

|     |     |     |     | 345 |     |     |     |     | 350 |     |     |     |     | 355 |     |      |
|-----|-----|-----|-----|-----|-----|-----|-----|-----|-----|-----|-----|-----|-----|-----|-----|------|
| TAC | TGT | GAG | GGA | GAG | TGC | GCC | TTC | CCT | CTG | AAC | TCC | TAC | ATG | AAC | GCC | 1219 |
| Tyr | Cys | Glu | Gly | Glu | Cys | Ala | Phe | Pro | Leu | Asn | Ser | Tyr | Met | Asn | Ala |      |
|     |     |     |     | 360 |     |     |     |     | 365 |     |     |     |     | 370 |     |      |

| ACC | AAC | CAC | GCC | ATC | GTC | CAG | ACA | CTG | GTT | CAC | TTC | ATC | AAC | CCA | GAC | 1267 |
| Thr | Asn | His | Ala | Ile | Val | Gln | Thr | Leu | Val | His | Phe | Ile | Asn | Pro | Asp |      |
|     |     | 375 |     |     |     |     | 380 |     |     |     |     | 385 |     |     |     |      |

| ACA | GTA | CCC | AAG | CCC | TGC | TGT | GCG | CCC | ACC | CAG | CTC | AAC | GCC | ATC | TCT | 1315 |
| Thr | Val | Pro | Lys | Pro | Cys | Cys | Ala | Pro | Thr | Gln | Leu | Asn | Ala | Ile | Ser |      |
|     | 390 |     |     |     |     | 395 |     |     |     |     | 400 |     |     |     |     |      |

| GTC | CTC | TAC | TTC | GAC | GAC | AGC | TCT | AAT | GTC | GAC | CTG | AAG | AAG | TAC | AGA | 1363 |
| Val | Leu | Tyr | Phe | Asp | Asp | Ser | Ser | Asn | Val | Asp | Leu | Lys | Lys | Tyr | Arg |      |
| 405 |     |     |     |     | 410 |     |     |     |     | 415 |     |     |     |     | 420 |      |

| AAC | ATG | GTG | GTC | CGG | GCC | TGT | GGC | TGC | CAC | TAGCTCTTCC | TGAGACCCTG |     |     |     |     | 1413 |
| Asn | Met | Val | Val | Arg | Ala | Cys | Gly | Cys | His |            |            |     |     |     |     |      |
|     |     |     |     | 425 |     |     |     | 430 |     |            |            |     |     |     |     |      |

```
ACCTTTGCGG GGCCACACCT TTCCAAATCT TCGATGTCTC ACCATCTAAG TCTCTCACTG    1473
CCCACCTTGG CGAGGAGAAC AGACCAACCT CTCCTGAGCC TTCCCTCACC TCCCAACCGG    1533
AAGCATGTAA GGGTTCCAGA AACCTGAGCG TGCAGCAGCT GATGAGCGCC CTTTCCTTCT    1593
GGCACGTGAC GGACAAGATC CTACCAGCTA CCACAGCAAA CGCCTAAGAG CAGGAAAAAT    1653
GTCTGCCAGG AAAGTGTCCA GTGTCCACAT GGCCCCTGGC GCTCTGAGTC TTTGAGGAGT    1713
AATCGCAAGC CTCGTTCAGC TGCAGCAGAA GGAAGGGCTT AGCCAGGGTG GCGCTGGCG    1773
TCTGTGTTGA AGGGAAACCA AGCAGAAGCC ACTGTAATGA TATGTCACAA TAAAACCCAT    1833
GAATGAAAAA AAAAAAAAAA AAAAAAAAAA AAAAGAATTC                           1873
```

( 2 ) INFORMATION FOR SEQ ID NO:9:

( i ) SEQUENCE CHARACTERISTICS:
        ( A ) LENGTH: 430 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| Met | His | Val | Arg | Ser | Leu | Arg | Ala | Ala | Pro | His | Ser | Phe | Val | Ala |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Leu | Trp | Ala | Pro | Leu | Phe | Leu | Leu | Arg | Ser | Ala | Leu | Ala | Asp | Phe | Ser |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Leu | Asp | Asn | Glu | Val | His | Ser | Ser | Phe | Ile | His | Arg | Arg | Leu | Arg | Ser |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Gln | Glu | Arg | Arg | Glu | Met | Gln | Arg | Glu | Ile | Leu | Ser | Ile | Leu | Gly | Leu |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Pro | His | Arg | Pro | Arg | Pro | His | Leu | Gln | Gly | Lys | His | Asn | Ser | Ala | Pro |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Met | Phe | Met | Leu | Asp | Leu | Tyr | Asn | Ala | Met | Ala | Val | Glu | Glu | Ser | Gly |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Pro | Asp | Gly | Gln | Gly | Phe | Ser | Tyr | Pro | Tyr | Lys | Ala | Val | Phe | Ser | Thr |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Gln | Gly | Pro | Pro | Leu | Ala | Ser | Leu | Gln | Asp | Ser | His | Phe | Leu | Thr | Asp |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Ala | Asp | Met | Val | Met | Ser | Phe | Val | Asn | Leu | Val | Glu | His | Asp | Lys | Glu |
|-----|-----|-----|-----|-----|-----|-----|-----|-----|-----|-----|-----|-----|-----|-----|-----|
| 130 |     |     |     |     | 135 |     |     |     |     | 140 |     |     |     |     |     |

| Phe | Phe | His | Pro | Arg | Tyr | His | His | Arg | Glu | Phe | Arg | Phe | Asp | Leu | Ser |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Lys | Ile | Pro | Glu | Gly | Glu | Arg | Val | Thr | Ala | Ala | Glu | Phe | Arg | Ile | Tyr |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| | | | | | | | | | | | | | | |
|---|---|---|---|---|---|---|---|---|---|---|---|---|---|---|
| Lys | Asp | Tyr | Ile<br>180 | Arg | Glu | Arg | Phe | Asp<br>185 | Asn | Glu | Thr | Phe | Gln<br>190 | Ile | Thr |
| Val | Tyr | Gln<br>195 | Val | Leu | Gln | Glu | His<br>200 | Ser | Gly | Arg | Glu | Ser<br>205 | Asp | Leu | Phe |
| Leu | Leu<br>210 | Asp | Ser | Arg | Thr | Ile<br>215 | Trp | Ala | Ser | Glu | Glu<br>220 | Gly | Trp | Leu | Val |
| Phe<br>225 | Asp | Ile | Thr | Ala | Thr<br>230 | Ser | Asn | His | Trp | Val<br>235 | Val | Asn | Pro | Arg | His<br>240 |
| Asn | Leu | Gly | Leu | Gln<br>245 | Leu | Ser | Val | Glu | Thr<br>250 | Leu | Asp | Gly | Gln | Ser<br>255 | Ile |
| Asn | Pro | Lys | Leu<br>260 | Ala | Gly | Leu | Ile | Gly<br>265 | Arg | His | Gly | Pro | Gln<br>270 | Asn | Lys |
| Gln | Pro | Phe<br>275 | Met | Val | Ala | Phe | Phe<br>280 | Lys | Ala | Thr | Glu | Val<br>285 | His | Leu | Arg |
| Ser | Ile<br>290 | Arg | Ser | Thr | Gly | Gly<br>295 | Lys | Gln | Arg | Ser | Gln<br>300 | Asn | Arg | Ser | Lys |
| Thr<br>305 | Pro | Lys | Asn | Gln | Glu<br>310 | Ala | Leu | Arg | Met | Ala<br>315 | Ser | Val | Ala | Glu | Asn<br>320 |
| Ser | Ser | Ser | Asp | Gln<br>325 | Arg | Gln | Ala | Cys | Lys<br>330 | Lys | His | Glu | Leu | Tyr<br>335 | Val |
| Ser | Phe | Arg | Asp<br>340 | Leu | Gly | Trp | Gln | Asp<br>345 | Trp | Ile | Ile | Ala | Pro<br>350 | Glu | Gly |
| Tyr | Ala | Ala<br>355 | Tyr | Tyr | Cys | Glu | Gly<br>360 | Glu | Cys | Ala | Phe | Pro<br>365 | Leu | Asn | Ser |
| Tyr | Met<br>370 | Asn | Ala | Thr | Asn | His<br>375 | Ala | Ile | Val | Gln | Thr<br>380 | Leu | Val | His | Phe |
| Ile<br>385 | Asn | Pro | Asp | Thr | Val<br>390 | Pro | Lys | Pro | Cys | Cys<br>395 | Ala | Pro | Thr | Gln | Leu<br>400 |
| Asn | Ala | Ile | Ser | Val<br>405 | Leu | Tyr | Phe | Asp | Asp<br>410 | Ser | Ser | Asn | Val | Asp<br>415 | Leu |
| Lys | Lys | Tyr | Arg<br>420 | Asn | Met | Val | Val | Arg<br>425 | Ala | Cys | Gly | Cys | His<br>430 | | |

( 2 ) INFORMATION FOR SEQ ID NO:10:

( i ) SEQUENCE CHARACTERISTICS:
        ( A ) LENGTH: 1723 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens
        ( F ) TISSUE TYPE: HIPPOCAMPUS ( i x ) FEATURE:
        ( A ) NAME/KEY: CDS
        ( B ) LOCATION: 490..1696
        ( D ) OTHER INFORMATION: /function="OSTEOGENIC PROTEIN"
                      / product="hOP2-PP"
                      / note="hOP2 (cDNA)"

( x i ) SEQUENCE DESCRIPTION: SEQ ID NO:10:

| | | | | | |
|---|---|---|---|---|---|
| GGCGCCGGCA | GAGCAGGAGT | GGCTGGAGGA | GCTGTGGTTG | GAGCAGGAGG | TGGCACGGCA    60 |
| GGGCTGGAGG | GCTCCCTATG | AGTGGCGGAG | ACGGCCCAGG | AGGCGCTGGA | GCAACAGCTC  120 |
| CCACACCGCA | CCAAGCGGTG | GCTGCAGGAG | CTCGCCCATC | GCCCTGCGC | TGCTCGGACC  180 |
| GCGGCCACAG | CCGGACTGGC | GGGTACGGCG | GCGACAGAGG | CATTGGCCGA | GAGTCCCAGT  240 |
| CCGCAGAGTA | GCCCCGGCCT | CGAGGCGGTG | GCGTCCCGGT | CCTCTCCGTC | CAGGAGCCAG  300 |

-continued

| | | | | | | |
|---|---|---|---|---|---|---|
| GACAGGTGTC | GCGCGGCGGG | GCTCCAGGGA | CCGCGCCTGA | GGCCGGCTGC | CCGCCCGTCC | 360 |
| CGCCCCGCCC | CGCCGCCCGC | CGCCCGCCGA | GCCCAGCCTC | CTTGCCGTCG | GGGCGTCCCC | 420 |
| AGGCCCTGGG | TCGGCCGCGG | AGCCGATGCG | CGCCCGCTGA | GCGCCCCAGC | TGAGCGCCCC | 480 |

```
CGGCCTGCC ATG ACC GCG CTC CCC GGC CCG CTC TGG CTC CTG GGC CTG           528
          Met Thr Ala Leu Pro Gly Pro Leu Trp Leu Leu Gly Leu
           1               5                    10

GCG CTA TGC GCG CTG GGC GGG GGC GGC CCC GGC CTG CGA CCC CCG CCC         576
Ala Leu Cys Ala Leu Gly Gly Gly Gly Pro Gly Leu Arg Pro Pro Pro
    15              20                  25

GGC TGT CCC CAG CGA CGT CTG GGC GCG CGC GAG CGC CGG GAC GTG CAG         624
Gly Cys Pro Gln Arg Arg Leu Gly Ala Arg Glu Arg Arg Asp Val Gln
30              35                  40                      45

CGC GAG ATC CTG GCG GTG CTC GGG CTG CCT GGG CGG CCC CGG CCC CGC         672
Arg Glu Ile Leu Ala Val Leu Gly Leu Pro Gly Arg Pro Arg Pro Arg
            50                  55                  60

GCG CCA CCC GCC GCC TCC CGG CTG CCC GCG TCC GCG CCG CTC TTC ATG         720
Ala Pro Pro Ala Ala Ser Arg Leu Pro Ala Ser Ala Pro Leu Phe Met
                65                  70                  75

CTG GAC CTG TAC CAC GCC ATG GCC GGC GAC GAC GAC GAG GAC GGC GCG         768
Leu Asp Leu Tyr His Ala Met Ala Gly Asp Asp Asp Glu Asp Gly Ala
            80                  85                  90

CCC GCG GAG CGG CGC CTG GGC CGC GCC GAC CTG GTC ATG AGC TTC GTT         816
Pro Ala Glu Arg Arg Leu Gly Arg Ala Asp Leu Val Met Ser Phe Val
        95                  100                 105

AAC ATG GTG GAG CGA GAC CGT GCC CTG GGC CAC CAG GAG CCC CAT TGG         864
Asn Met Val Glu Arg Asp Arg Ala Leu Gly His Gln Glu Pro His Trp
110                 115                 120                 125

AAG GAG TTC CGC TTT GAC CTG ACC CAG ATC CCG GCT GGG GAG GCG GTC         912
Lys Glu Phe Arg Phe Asp Leu Thr Gln Ile Pro Ala Gly Glu Ala Val
                130                 135                 140

ACA GCT GCG GAG TTC CGG ATT TAC AAG GTG CCC AGC ATC CAC CTG CTC         960
Thr Ala Ala Glu Phe Arg Ile Tyr Lys Val Pro Ser Ile His Leu Leu
                145                 150                 155

AAC AGG ACC CTC CAC GTC AGC ATG TTC CAG GTG GTC CAG GAG CAG TCC        1008
Asn Arg Thr Leu His Val Ser Met Phe Gln Val Val Gln Glu Gln Ser
        160                 165                 170

AAC AGG GAG TCT GAC TTG TTC TTT TTG GAT CTT CAG ACG CTC CGA GCT        1056
Asn Arg Glu Ser Asp Leu Phe Phe Leu Asp Leu Gln Thr Leu Arg Ala
175                 180                 185

GGA GAC GAG GGC TGG CTG GTG CTG GAT GTC ACA GCA GCC AGT GAC TGC        1104
Gly Asp Glu Gly Trp Leu Val Leu Asp Val Thr Ala Ala Ser Asp Cys
190                 195                 200                 205

TGG TTG CTG AAG CGT CAC AAG GAC CTG GGA CTC CGC CTC TAT GTG GAG        1152
Trp Leu Leu Lys Arg His Lys Asp Leu Gly Leu Arg Leu Tyr Val Glu
                210                 215                 220

ACT GAG GAC GGG CAC AGC GTG GAT CCT GGC CTG GCC GGC CTG CTG GGT        1200
Thr Glu Asp Gly His Ser Val Asp Pro Gly Leu Ala Gly Leu Leu Gly
                225                 230                 235

CAA CGG GCC CCA CGC TCC CAA CAG CCT TTC GTG GTC ACT TTC TTC AGG        1248
Gln Arg Ala Pro Arg Ser Gln Gln Pro Phe Val Val Thr Phe Phe Arg
            240                 245                 250

GCC AGT CCG AGT CCC ATC CGC ACC CCT CGG GCA GTG AGG CCA CTG AGG        1296
Ala Ser Pro Ser Pro Ile Arg Thr Pro Arg Ala Val Arg Pro Leu Arg
255                 260                 265

AGG AGG CAG CCG AAG AAA AGC AAC GAG CTG CCG CAG GCC AAC CGA CTC        1344
Arg Arg Gln Pro Lys Lys Ser Asn Glu Leu Pro Gln Ala Asn Arg Leu
270                 275                 280                 285

CCA GGG ATC TTT GAT GAC GTC CAC GGC TCC CAC GGC CGG CAG GTC TGC        1392
Pro Gly Ile Phe Asp Asp Val His Gly Ser His Gly Arg Gln Val Cys
        290                 295                 300
```

|  |  |  |  |  |  |  |  |  |  |  |  |  |  |  |  |
|---|---|---|---|---|---|---|---|---|---|---|---|---|---|---|---|
| CGT | CGG | CAC | GAG | CTC | TAC | GTC | AGC | TTC | CAG | GAC | CTC | GGC | TGG | CTG | GAC | 1440
| Arg | Arg | His | Glu | Leu | Tyr | Val | Ser | Phe | Gln | Asp | Leu | Gly | Trp | Leu | Asp |
|  |  | 305 |  |  |  |  | 310 |  |  |  |  | 315 |  |  |  |
| TGG | GTC | ATC | GCT | CCC | CAA | GGC | TAC | TCG | GCC | TAT | TAC | TGT | GAG | GGG | GAG | 1488
| Trp | Val | Ile | Ala | Pro | Gln | Gly | Tyr | Ser | Ala | Tyr | Tyr | Cys | Glu | Gly | Glu |
|  |  | 320 |  |  |  |  | 325 |  |  |  |  | 330 |  |  |  |
| TGC | TCC | TTC | CCA | CTG | GAC | TCC | TGC | ATG | AAT | GCC | ACC | AAC | CAC | GCC | ATC | 1536
| Cys | Ser | Phe | Pro | Leu | Asp | Ser | Cys | Met | Asn | Ala | Thr | Asn | His | Ala | Ile |
|  | 335 |  |  |  |  | 340 |  |  |  |  | 345 |  |  |  |  |
| CTG | CAG | TCC | CTG | GTG | CAC | CTG | ATG | AAG | CCA | AAC | GCA | GTC | CCC | AAG | GCG | 1584
| Leu | Gln | Ser | Leu | Val | His | Leu | Met | Lys | Pro | Asn | Ala | Val | Pro | Lys | Ala |
| 350 |  |  |  |  | 355 |  |  |  |  | 360 |  |  |  |  | 365 |
| TGC | TGT | GCA | CCC | ACC | AAG | CTG | AGC | GCC | ACC | TCT | GTG | CTC | TAC | TAT | GAC | 1632
| Cys | Cys | Ala | Pro | Thr | Lys | Leu | Ser | Ala | Thr | Ser | Val | Leu | Tyr | Tyr | Asp |
|  |  |  | 370 |  |  |  |  | 375 |  |  |  |  | 380 |  |  |
| AGC | AGC | AAC | AAC | GTC | ATC | CTG | CGC | AAA | GCC | CGC | AAC | ATG | GTG | GTC | AAG | 1680
| Ser | Ser | Asn | Asn | Val | Ile | Leu | Arg | Lys | Ala | Arg | Asn | Met | Val | Val | Lys |
|  |  | 385 |  |  |  |  | 390 |  |  |  |  | 395 |  |  |  |
| GCC | TGC | GGC | TGC | CAC | T GAGTCAGCCC | GCCCAGCCCT | ACTGCAG |  |  |  |  |  |  |  |  | 1723
| Ala | Cys | Gly | Cys | His |  |  |  |  |  |  |  |  |  |  |  |
|  |  | 400 |  |  |  |  |  |  |  |  |  |  |  |  |  |

( 2 ) INFORMATION FOR SEQ ID NO:11:

( i ) SEQUENCE CHARACTERISTICS:
        ( A ) LENGTH: 402 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

|  |  |  |  |  |  |  |  |  |  |  |  |  |  |  |  |
|---|---|---|---|---|---|---|---|---|---|---|---|---|---|---|---|
| Met | Thr | Ala | Leu | Pro | Gly | Pro | Leu | Trp | Leu | Leu | Gly | Leu | Ala | Leu | Cys |
| 1 |  |  |  | 5 |  |  |  | 10 |  |  |  |  |  | 15 |  |
| Ala | Leu | Gly | Gly | Gly | Gly | Pro | Gly | Leu | Arg | Pro | Pro | Pro | Gly | Cys | Pro |
|  |  |  | 20 |  |  |  |  | 25 |  |  |  |  | 30 |  |  |
| Gln | Arg | Arg | Leu | Gly | Ala | Arg | Glu | Arg | Arg | Asp | Val | Gln | Arg | Glu | Ile |
|  |  |  | 35 |  |  |  |  | 40 |  |  |  |  | 45 |  |  |
| Leu | Ala | Val | Leu | Gly | Leu | Pro | Gly | Arg | Pro | Arg | Pro | Arg | Ala | Pro | Pro |
|  | 50 |  |  |  |  | 55 |  |  |  |  | 60 |  |  |  |  |
| Ala | Ala | Ser | Arg | Leu | Pro | Ala | Ser | Ala | Pro | Leu | Phe | Met | Leu | Asp | Leu |
| 65 |  |  |  |  | 70 |  |  |  |  | 75 |  |  |  |  | 80 |
| Tyr | His | Ala | Met | Ala | Gly | Asp | Asp | Asp | Glu | Asp | Gly | Ala | Pro | Ala | Glu |
|  |  |  |  | 85 |  |  |  |  | 90 |  |  |  |  | 95 |  |
| Arg | Arg | Leu | Gly | Arg | Ala | Asp | Leu | Val | Met | Ser | Phe | Val | Asn | Met | Val |
|  |  |  | 100 |  |  |  |  | 105 |  |  |  |  | 110 |  |  |
| Glu | Arg | Asp | Arg | Ala | Leu | Gly | His | Gln | Glu | Pro | His | Trp | Lys | Glu | Phe |
|  |  | 115 |  |  |  |  | 120 |  |  |  |  | 125 |  |  |  |
| Arg | Phe | Asp | Leu | Thr | Gln | Ile | Pro | Ala | Gly | Glu | Ala | Val | Thr | Ala | Ala |
|  | 130 |  |  |  |  | 135 |  |  |  |  | 140 |  |  |  |  |
| Glu | Phe | Arg | Ile | Tyr | Lys | Val | Pro | Ser | Ile | His | Leu | Leu | Asn | Arg | Thr |
| 145 |  |  |  |  | 150 |  |  |  |  | 155 |  |  |  |  | 160 |
| Leu | His | Val | Ser | Met | Phe | Gln | Val | Val | Gln | Glu | Gln | Ser | Asn | Arg | Glu |
|  |  |  |  | 165 |  |  |  |  | 170 |  |  |  |  | 175 |  |
| Ser | Asp | Leu | Phe | Phe | Leu | Asp | Leu | Gln | Thr | Leu | Arg | Ala | Gly | Asp | Glu |
|  |  |  | 180 |  |  |  |  | 185 |  |  |  |  | 190 |  |  |
| Gly | Trp | Leu | Val | Leu | Asp | Val | Thr | Ala | Ala | Ser | Asp | Cys | Trp | Leu | Leu |
|  |  | 195 |  |  |  |  | 200 |  |  |  |  | 205 |  |  |  |
| Lys | Arg | His | Lys | Asp | Leu | Gly | Leu | Arg | Leu | Tyr | Val | Glu | Thr | Glu | Asp |
| 210 |  |  |  |  | 215 |  |  |  |  | 220 |  |  |  |  |  |

| | | | | | | | | | | | | | | | |
|---|---|---|---|---|---|---|---|---|---|---|---|---|---|---|---|
|Gly|His|Ser|Val|Asp|Pro|Gly|Leu|Ala|Gly|Leu|Leu|Gly|Gln|Arg|Ala|
|225| | | |230| | | |235| | | | | | |240|
|Pro|Arg|Ser|Gln|Gln|Pro|Phe|Val|Val|Thr|Phe|Phe|Arg|Ala|Ser|Pro|
| | | |245| | | | |250| | | | |255| | |
|Ser|Pro|Ile|Arg|Thr|Pro|Arg|Ala|Val|Arg|Pro|Leu|Arg|Arg|Arg|Gln|
| | | |260| | | | |265| | | |270| | | |
|Pro|Lys|Lys|Ser|Asn|Glu|Leu|Pro|Gln|Ala|Asn|Arg|Leu|Pro|Gly|Ile|
| | |275| | | | |280| | | | |285| | | |
|Phe|Asp|Asp|Val|His|Gly|Ser|His|Gly|Arg|Gln|Val|Cys|Arg|Arg|His|
| |290| | | |295| | | | |300| | | | | |
|Glu|Leu|Tyr|Val|Ser|Phe|Gln|Asp|Leu|Gly|Trp|Leu|Asp|Trp|Val|Ile|
|305| | | | |310| | | |315| | | | | |320|
|Ala|Pro|Gln|Gly|Tyr|Ser|Ala|Tyr|Tyr|Cys|Glu|Gly|Glu|Cys|Ser|Phe|
| | | | |325| | | |330| | | | |335| | |
|Pro|Leu|Asp|Ser|Cys|Met|Asn|Ala|Thr|Asn|His|Ala|Ile|Leu|Gln|Ser|
| | | |340| | | | |345| | | | |350| | |
|Leu|Val|His|Leu|Met|Lys|Pro|Asn|Ala|Val|Pro|Lys|Ala|Cys|Cys|Ala|
| | |355| | | | |360| | | | |365| | | |
|Pro|Thr|Lys|Leu|Ser|Ala|Thr|Ser|Val|Leu|Tyr|Tyr|Asp|Ser|Ser|Asn|
| |370| | | | |375| | | | |380| | | | |
|Asn|Val|Ile|Leu|Arg|Lys|Ala|Arg|Asn|Met|Val|Val|Lys|Ala|Cys|Gly|
|385| | | | |390| | | | |395| | | | |400|
|Cys|His| | | | | | | | | | | | | | |

( 2 ) INFORMATION FOR SEQ ID NO:12:

( i ) SEQUENCE CHARACTERISTICS:
        ( A ) LENGTH: 1926 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: MURIDAE
        ( F ) TISSUE TYPE: EMBRYO ( i x ) FEATURE:
        ( A ) NAME/KEY: CDS
        ( B ) LOCATION: 93..1289
        ( D ) OTHER INFORMATION: /function="OSTEOGENIC PROTEIN"
            / product="mOP2-PP"
            / note="mOP2 cDNA"

( x i ) SEQUENCE DESCRIPTION: SEQ ID NO:12:

```
GCCAGGCACA  GGTGCGCCGT  CTGGTCCTCC  CCGTCTGGCG  TCAGCCGAGC  CCGACCAGCT         60

ACCAGTGGAT  GCGCGCCGGC  TGAAAGTCCG  AG ATG GCT ATG CGT CCC GGG CCA            113
                                      Met Ala Met Arg Pro Gly Pro
                                       1           5
```

| CTC | TGG | CTA | TTG | GGC | CTT | GCT | CTG | TGC | GCG | CTG | GGA | GGC | GGC | CAC | GGT | 161 |
|---|---|---|---|---|---|---|---|---|---|---|---|---|---|---|---|---|
| Leu | Trp | Leu | Leu | Gly | Leu | Ala | Leu | Cys | Ala | Leu | Gly | Gly | Gly | His | Gly | |
| | | 10 | | | | | 15 | | | | | 20 | | | | |

| CCG | CGT | CCC | CCG | CAC | ACC | TGT | CCC | CAG | CGT | CGC | CTG | GGA | GCG | CGC | GAG | 209 |
|---|---|---|---|---|---|---|---|---|---|---|---|---|---|---|---|---|
| Pro | Arg | Pro | Pro | His | Thr | Cys | Pro | Gln | Arg | Arg | Leu | Gly | Ala | Arg | Glu | |
| | 25 | | | | 30 | | | | | 35 | | | | | | |

| CGC | CGC | GAC | ATG | CAG | CGT | GAA | ATC | CTG | GCG | GTG | CTC | GGG | CTA | CCG | GGA | 257 |
|---|---|---|---|---|---|---|---|---|---|---|---|---|---|---|---|---|
| Arg | Arg | Asp | Met | Gln | Arg | Glu | Ile | Leu | Ala | Val | Leu | Gly | Leu | Pro | Gly | |
| 40 | | | | 45 | | | | 50 | | | | | 55 | | | |

| CGG | CCC | CGA | CCC | CGT | GCA | CAA | CCC | GCC | GCT | GCC | CGG | CAG | CCA | GCG | TCC | 305 |
|---|---|---|---|---|---|---|---|---|---|---|---|---|---|---|---|---|
| Arg | Pro | Arg | Pro | Arg | Ala | Gln | Pro | Ala | Ala | Ala | Arg | Gln | Pro | Ala | Ser | |
| | | | | 60 | | | | 65 | | | | | 70 | | | |

| GCG | CCC | CTC | TTC | ATG | TTG | GAC | CTA | TAC | CAC | GCC | ATG | ACC | GAT | GAC | GAC | 353 |
|---|---|---|---|---|---|---|---|---|---|---|---|---|---|---|---|---|
| Ala | Pro | Leu | Phe | Met | Leu | Asp | Leu | Tyr | His | Ala | Met | Thr | Asp | Asp | Asp | |

|  |  |  |  |  |  |  |  |  |  |  |  |  |  |  |  |  |
|--|--|--|--|--|--|--|--|--|--|--|--|--|--|--|--|--|
|  |  | 75 |  |  |  |  | 80 |  |  |  |  | 85 |  |  |  |  |
| GAC | GGC | GGG | CCA | CCA | CAG | GCT | CAC | TTA | GGC | CGT | GCC | GAC | CTG | GTC | ATG | 401 |
| Asp | Gly | Gly | Pro | Pro | Gln | Ala | His | Leu | Gly | Arg | Ala | Asp | Leu | Val | Met |  |
|  |  | 90 |  |  |  |  | 95 |  |  |  |  | 100 |  |  |  |  |
| AGC | TTC | GTC | AAC | ATG | GTG | GAA | CGC | GAC | CGT | ACC | CTG | GGC | TAC | CAG | GAG | 449 |
| Ser | Phe | Val | Asn | Met | Val | Glu | Arg | Asp | Arg | Thr | Leu | Gly | Tyr | Gln | Glu |  |
|  |  | 105 |  |  |  |  | 110 |  |  |  |  | 115 |  |  |  |  |
| CCA | CAC | TGG | AAG | GAA | TTC | CAC | TTT | GAC | CTA | ACC | CAG | ATC | CCT | GCT | GGG | 497 |
| Pro | His | Trp | Lys | Glu | Phe | His | Phe | Asp | Leu | Thr | Gln | Ile | Pro | Ala | Gly |  |
| 120 |  |  |  |  | 125 |  |  |  |  | 130 |  |  |  |  | 135 |  |
| GAG | GCT | GTC | ACA | GCT | GCT | GAG | TTC | CGG | ATC | TAC | AAA | GAA | CCC | AGC | ACC | 545 |
| Glu | Ala | Val | Thr | Ala | Ala | Glu | Phe | Arg | Ile | Tyr | Lys | Glu | Pro | Ser | Thr |  |
|  |  |  |  | 140 |  |  |  |  | 145 |  |  |  |  | 150 |  |  |
| CAC | CCG | CTC | AAC | ACA | ACC | CTC | CAC | ATC | AGC | ATG | TTC | GAA | GTG | GTC | CAA | 593 |
| His | Pro | Leu | Asn | Thr | Thr | Leu | His | Ile | Ser | Met | Phe | Glu | Val | Val | Gln |  |
|  |  |  | 155 |  |  |  |  | 160 |  |  |  |  | 165 |  |  |  |
| GAG | CAC | TCC | AAC | AGG | GAG | TCT | GAC | TTG | TTC | TTT | TTG | GAT | CTT | CAG | ACG | 641 |
| Glu | His | Ser | Asn | Arg | Glu | Ser | Asp | Leu | Phe | Phe | Leu | Asp | Leu | Gln | Thr |  |
|  |  | 170 |  |  |  |  | 175 |  |  |  |  | 180 |  |  |  |  |
| CTC | CGA | TCT | GGG | GAC | GAG | GGC | TGG | CTG | GTG | CTG | GAC | ATC | ACA | GCA | GCC | 689 |
| Leu | Arg | Ser | Gly | Asp | Glu | Gly | Trp | Leu | Val | Leu | Asp | Ile | Thr | Ala | Ala |  |
|  | 185 |  |  |  |  | 190 |  |  |  |  | 195 |  |  |  |  |  |
| AGT | GAC | CGA | TGG | CTG | CTG | AAC | CAT | CAC | AAG | GAC | CTG | GGA | CTC | CGC | CTC | 737 |
| Ser | Asp | Arg | Trp | Leu | Leu | Asn | His | His | Lys | Asp | Leu | Gly | Leu | Arg | Leu |  |
| 200 |  |  |  |  | 205 |  |  |  |  | 210 |  |  |  |  | 215 |  |
| TAT | GTG | GAA | ACC | GCG | GAT | GGG | CAC | AGC | ATG | GAT | CCT | GGC | CTG | GCT | GGT | 785 |
| Tyr | Val | Glu | Thr | Ala | Asp | Gly | His | Ser | Met | Asp | Pro | Gly | Leu | Ala | Gly |  |
|  |  |  |  | 220 |  |  |  |  | 225 |  |  |  |  | 230 |  |  |
| CTG | CTT | GGA | CGA | CAA | GCA | CCA | CGC | TCC | AGA | CAG | CCT | TTC | ATG | GTA | ACC | 833 |
| Leu | Leu | Gly | Arg | Gln | Ala | Pro | Arg | Ser | Arg | Gln | Pro | Phe | Met | Val | Thr |  |
|  |  |  | 235 |  |  |  |  | 240 |  |  |  |  | 245 |  |  |  |
| TTC | TTC | AGG | GCC | AGC | CAG | AGT | CCT | GTG | CGG | GCC | CCT | CGG | GCA | GCG | AGA | 881 |
| Phe | Phe | Arg | Ala | Ser | Gln | Ser | Pro | Val | Arg | Ala | Pro | Arg | Ala | Ala | Arg |  |
|  |  | 250 |  |  |  |  | 255 |  |  |  |  | 260 |  |  |  |  |
| CCA | CTG | AAG | AGG | AGG | CAG | CCA | AAG | AAA | ACG | AAC | GAG | CTT | CCG | CAC | CCC | 929 |
| Pro | Leu | Lys | Arg | Arg | Gln | Pro | Lys | Lys | Thr | Asn | Glu | Leu | Pro | His | Pro |  |
|  | 265 |  |  |  |  | 270 |  |  |  |  | 275 |  |  |  |  |  |
| AAC | AAA | CTC | CCA | GGG | ATC | TTT | GAT | GAT | GGC | CAC | GGT | TCC | CGC | GGC | AGA | 977 |
| Asn | Lys | Leu | Pro | Gly | Ile | Phe | Asp | Asp | Gly | His | Gly | Ser | Arg | Gly | Arg |  |
| 280 |  |  |  |  | 285 |  |  |  |  | 290 |  |  |  |  | 295 |  |
| GAG | GTT | TGC | CGC | AGG | CAT | GAG | CTC | TAC | GTC | AGC | TTC | CGT | GAC | CTT | GGC | 1025 |
| Glu | Val | Cys | Arg | Arg | His | Glu | Leu | Tyr | Val | Ser | Phe | Arg | Asp | Leu | Gly |  |
|  |  |  |  | 300 |  |  |  |  | 305 |  |  |  |  | 310 |  |  |
| TGG | CTG | GAC | TGG | GTC | ATC | GCC | CCC | CAG | GGC | TAC | TCT | GCC | TAT | TAC | TGT | 1073 |
| Trp | Leu | Asp | Trp | Val | Ile | Ala | Pro | Gln | Gly | Tyr | Ser | Ala | Tyr | Tyr | Cys |  |
|  |  |  | 315 |  |  |  |  | 320 |  |  |  |  | 325 |  |  |  |
| GAG | GGG | GAG | TGT | GCT | TTC | CCA | CTG | GAC | TCC | TGT | ATG | AAC | GCC | ACC | AAC | 1121 |
| Glu | Gly | Glu | Cys | Ala | Phe | Pro | Leu | Asp | Ser | Cys | Met | Asn | Ala | Thr | Asn |  |
|  |  | 330 |  |  |  |  | 335 |  |  |  |  | 340 |  |  |  |  |
| CAT | GCC | ATC | TTG | CAG | TCT | CTG | GTG | CAC | CTG | ATG | AAG | CCA | GAT | GTT | GTC | 1169 |
| His | Ala | Ile | Leu | Gln | Ser | Leu | Val | His | Leu | Met | Lys | Pro | Asp | Val | Val |  |
|  | 345 |  |  |  |  | 350 |  |  |  |  | 355 |  |  |  |  |  |
| CCC | AAG | GCA | TGC | TGT | GCA | CCC | ACC | AAA | CTG | AGT | GCC | ACC | TCT | GTG | CTG | 1217 |
| Pro | Lys | Ala | Cys | Cys | Ala | Pro | Thr | Lys | Leu | Ser | Ala | Thr | Ser | Val | Leu |  |
| 360 |  |  |  |  | 365 |  |  |  |  | 370 |  |  |  |  | 375 |  |
| TAC | TAT | GAC | AGC | AGC | AAC | AAT | GTC | ATC | CTG | CGT | AAA | CAC | CGT | AAC | ATG | 1265 |
| Tyr | Tyr | Asp | Ser | Ser | Asn | Asn | Val | Ile | Leu | Arg | Lys | His | Arg | Asn | Met |  |
|  |  |  |  | 380 |  |  |  |  | 385 |  |  |  |  | 390 |  |  |
| GTG | GTC | AAG | GCC | TGT | GGC | TGC | CAC | TGAGGCCCCG | CCCAGCATCC | TGCTTCTACT |  |  |  |  |  | 1319 |
| Val | Val | Lys | Ala | Cys | Gly | Cys | His |  |  |  |  |  |  |  |  |  |
|  |  |  | 395 |  |  |  |  |  |  |  |  |  |  |  |  |  |

| | | | | |
|---|---|---|---|---|
|ACCTTACCAT|CTGGCCGGGC|CCCTCTCCAG|AGGCAGAAAC|CCTTCTATGT TATCATAGCT 1379|
|CAGACAGGGG|CAATGGGAGG|CCCTTCACTT|CCCCTGGCCA|CTTCCTGCTA AAATTCTGGT 1439|
|CTTTCCCAGT|TCCTCTGTCC|TTCATGGGGT|TTCGGGGCTA|TCACCCCGCC CTCTCCATCC 1499|
|TCCTACCCCA|AGCATAGACT|GAATGCACAC|AGCATCCAG|AGCTATGCTA ACTGAGAGGT 1559|
|CTGGGGTCAG|CACTGAAGGC|CCACATGAGG|AAGACTGATC|CTTGGCCATC CTCAGCCCAC 1619|
|AATGGCAAAT|TCTGGATGGT|CTAAGAAGGC|CCTGGAATTC|TAAACTAGAT GATCTGGGCT 1679|
|CTCTGCACCA|TTCATTGTGG|CAGTTGGGAC|ATTTTTAGGT|ATAACAGACA CATACACTTA 1739|
|GATCAATGCA|TCGCTGTACT|CCTTGAAATC|AGAGCTAGCT|TGTTAGAAAA AGAATCAGAG 1799|
|CCAGGTATAG|CGGTGCATGT|CATTAATCCC|AGCGCTAAAG|AGACAGAGAC AGGAGAATCT 1859|
|CTGTGAGTTC|AAGGCCACAT|AGAAAGAGCC|TGTCTCGGGA|GCAGGAAAAA AAAAAAAAAC 1919|
|GGAATTC| | | |1926|

( 2 ) INFORMATION FOR SEQ ID NO:13:

( i ) SEQUENCE CHARACTERISTICS:
        ( A ) LENGTH: 399 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Met Ala Met Arg Pro Gly Pro Leu Trp Leu Gly Leu Ala Leu Cys
 1               5                  10                  15
Ala Leu Gly Gly Gly His Gly Pro Arg Pro His Thr Cys Pro Gln
                20                  25                  30
Arg Arg Leu Gly Ala Arg Glu Arg Arg Asp Met Gln Arg Glu Ile Leu
            35                  40                  45
Ala Val Leu Gly Leu Pro Gly Arg Pro Arg Pro Arg Ala Gln Pro Ala
        50                  55                  60
Ala Ala Arg Gln Pro Ala Ser Ala Pro Leu Phe Met Leu Asp Leu Tyr
65                  70                  75                  80
His Ala Met Thr Asp Asp Asp Asp Gly Gly Pro Pro Gln Ala His Leu
                85                  90                  95
Gly Arg Ala Asp Leu Val Met Ser Phe Val Asn Met Val Glu Arg Asp
                100                 105                 110
Arg Thr Leu Gly Tyr Gln Glu Pro His Trp Lys Glu Phe His Phe Asp
            115                 120                 125
Leu Thr Gln Ile Pro Ala Gly Glu Ala Val Thr Ala Ala Glu Phe Arg
    130                 135                 140
Ile Tyr Lys Glu Pro Ser Thr His Pro Leu Asn Thr Thr Leu His Ile
145                 150                 155                 160
Ser Met Phe Glu Val Val Gln Glu His Ser Asn Arg Glu Ser Asp Leu
                165                 170                 175
Phe Phe Leu Asp Leu Gln Thr Leu Arg Ser Gly Asp Glu Gly Trp Leu
                180                 185                 190
Val Leu Asp Ile Thr Ala Ala Ser Asp Arg Trp Leu Leu Asn His His
            195                 200                 205
Lys Asp Leu Gly Leu Arg Leu Tyr Val Glu Thr Ala Asp Gly His Ser
    210                 215                 220
Met Asp Pro Gly Leu Ala Gly Leu Leu Gly Arg Gln Ala Pro Arg Ser
225                 230                 235                 240
Arg Gln Pro Phe Met Val Thr Phe Phe Arg Ala Ser Gln Ser Pro Val
                245                 250                 255
```

|     |     |     |     |     |     |     |     |     |     |     |     |     |     |     |
|-----|-----|-----|-----|-----|-----|-----|-----|-----|-----|-----|-----|-----|-----|-----|
| Arg | Ala | Pro | Arg | Ala | Ala | Arg | Pro | Leu | Lys | Arg | Arg | Gln | Pro | Lys | Lys |
|     |     | 260 |     |     |     |     | 265 |     |     |     |     | 270 |     |     |
| Thr | Asn | Glu | Leu | Pro | His | Pro | Asn | Lys | Leu | Pro | Gly | Ile | Phe | Asp | Asp |
|     |     | 275 |     |     |     |     | 280 |     |     |     |     | 285 |     |     |
| Gly | His | Gly | Ser | Arg | Gly | Arg | Glu | Val | Cys | Arg | Arg | His | Glu | Leu | Tyr |
|     | 290 |     |     |     |     | 295 |     |     |     |     |     | 300 |     |     |
| Val | Ser | Phe | Arg | Asp | Leu | Gly | Trp | Leu | Asp | Trp | Val | Ile | Ala | Pro | Gln |
| 305 |     |     |     |     | 310 |     |     |     |     | 315 |     |     |     |     | 320 |
| Gly | Tyr | Ser | Ala | Tyr | Tyr | Cys | Glu | Gly | Cys | Ala | Phe | Pro | Leu | Asp |
|     |     |     |     | 325 |     |     |     | 330 |     |     |     |     | 335 |     |
| Ser | Cys | Met | Asn | Ala | Thr | Asn | His | Ala | Ile | Leu | Gln | Ser | Leu | Val | His |
|     |     |     | 340 |     |     |     |     | 345 |     |     |     |     | 350 |     |     |
| Leu | Met | Lys | Pro | Asp | Val | Val | Pro | Lys | Ala | Cys | Cys | Ala | Pro | Thr | Lys |
|     |     | 355 |     |     |     |     | 360 |     |     |     |     | 365 |     |     |     |
| Leu | Ser | Ala | Thr | Ser | Val | Leu | Tyr | Tyr | Asp | Ser | Ser | Asn | Asn | Val | Ile |
|     | 370 |     |     |     |     | 375 |     |     |     |     | 380 |     |     |     |     |
| Leu | Arg | Lys | His | Arg | Asn | Met | Val | Val | Lys | Ala | Cys | Gly | Cys | His |
| 385 |     |     |     |     | 390 |     |     |     |     | 395 |     |     |     |     |

( 2 ) INFORMATION FOR SEQ ID NO:14:

( i ) SEQUENCE CHARACTERISTICS:
        ( A ) LENGTH: 1260 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: HOMO SAPIENS ( i x ) FEATURE:
        ( A ) NAME/KEY: CDS
        ( B ) LOCATION: 9..1196
        ( D ) OTHER INFORMATION: /function="OSTEOGENIC PROTEIN"
            / product="BMP2A"
            / note="BMP2A (CDNA)"

( x i ) SEQUENCE DESCRIPTION: SEQ ID NO:14:

```
GGTCGACC ATG GTG GCC GGG ACC CGC TGT CTT CTA GCG TTG CTG CTT CCC        50
         Met Val Ala Gly Thr Arg Cys Leu Leu Ala Leu Leu Leu Pro
         1               5                   10

CAG GTC CTC CTG GGC GGC GCG GCT GGC CTC GTT CCG GAG CTG GGC CGC        98
Gln Val Leu Leu Gly Gly Ala Ala Gly Leu Val Pro Glu Leu Gly Arg
15              20                  25                  30

AGG AAG TTC GCG GCG GCG TCG TCG GGC CGC CCC TCA TCC CAG CCC TCT       146
Arg Lys Phe Ala Ala Ala Ser Ser Gly Arg Pro Ser Ser Gln Pro Ser
            35                  40                  45

GAC GAG GTC CTG AGC GAG TTC GAG TTG CGG CTG CTC AGC ATG TTC GGC       194
Asp Glu Val Leu Ser Glu Phe Glu Leu Arg Leu Leu Ser Met Phe Gly
                50                  55                  60

CTG AAA CAG AGA CCC ACC CCC AGC AGG GAC GCC GTG GTG CCC CCC TAC       242
Leu Lys Gln Arg Pro Thr Pro Ser Arg Asp Ala Val Val Pro Pro Tyr
        65                  70                  75

ATG CTA GAC CTG TAT CGC AGG CAC TCG GGT CAG CCG GGC TCA CCC GCC       290
Met Leu Asp Leu Tyr Arg Arg His Ser Gly Gln Pro Gly Ser Pro Ala
        80                  85                  90

CCA GAC CAC CGG TTG GAG AGG GCA GCC AGC CGA GCC AAC ACT GTG CGC       338
Pro Asp His Arg Leu Glu Arg Ala Ala Ser Arg Ala Asn Thr Val Arg
95                  100                 105                 110
```

| | | | | | | | | | | | | | | | | |
|---|---|---|---|---|---|---|---|---|---|---|---|---|---|---|---|---|
| AGC | TTC | CAC | CAT | GAA | GAA | TCT | TTG | GAA | GAA | CTA | CCA | GAA | ACG | AGT | GGG | 386 |
| Ser | Phe | His | His | Glu | Glu | Ser | Leu | Glu | Glu | Leu | Pro | Glu | Thr | Ser | Gly | |
| | | | | 115 | | | | | 120 | | | | | 125 | | |
| AAA | ACA | ACC | CGG | AGA | TTC | TTC | TTT | AAT | TTA | AGT | TCT | ATC | CCC | ACG | GAG | 434 |
| Lys | Thr | Thr | Arg | Arg | Phe | Phe | Phe | Asn | Leu | Ser | Ser | Ile | Pro | Thr | Glu | |
| | | | 130 | | | | | 135 | | | | | 140 | | | |
| GAG | TTT | ATC | ACC | TCA | GCA | GAG | CTT | CAG | GTT | TTC | CGA | GAA | CAG | ATG | CAA | 482 |
| Glu | Phe | Ile | Thr | Ser | Ala | Glu | Leu | Gln | Val | Phe | Arg | Glu | Gln | Met | Gln | |
| | | 145 | | | | | 150 | | | | | 155 | | | | |
| GAT | GCT | TTA | GGA | AAC | AAT | AGC | AGT | TTC | CAT | CAC | CGA | ATT | AAT | ATT | TAT | 530 |
| Asp | Ala | Leu | Gly | Asn | Asn | Ser | Ser | Phe | His | His | Arg | Ile | Asn | Ile | Tyr | |
| | 160 | | | | | 165 | | | | | 170 | | | | | |
| GAA | ATC | ATA | AAA | CCT | GCA | ACA | GCC | AAC | TCG | AAA | TTC | CCC | GTG | ACC | AGT | 578 |
| Glu | Ile | Ile | Lys | Pro | Ala | Thr | Ala | Asn | Ser | Lys | Phe | Pro | Val | Thr | Ser | |
| 175 | | | | | 180 | | | | | 185 | | | | | 190 | |
| CTT | TTG | GAC | ACC | AGG | TTG | GTG | AAT | CAG | AAT | GCA | AGC | AGG | TGG | GAA | AGT | 626 |
| Leu | Leu | Asp | Thr | Arg | Leu | Val | Asn | Gln | Asn | Ala | Ser | Arg | Trp | Glu | Ser | |
| | | | | 195 | | | | | 200 | | | | | 205 | | |
| TTT | GAT | GTC | ACC | CCC | GCT | GTG | ATG | CGG | TGG | ACT | GCA | CAG | GGA | CAC | GCC | 674 |
| Phe | Asp | Val | Thr | Pro | Ala | Val | Met | Arg | Trp | Thr | Ala | Gln | Gly | His | Ala | |
| | | | 210 | | | | | 215 | | | | | 220 | | | |
| AAC | CAT | GGA | TTC | GTG | GTG | GAA | GTG | GCC | CAC | TTG | GAG | GAG | AAA | CAA | GGT | 722 |
| Asn | His | Gly | Phe | Val | Val | Glu | Val | Ala | His | Leu | Glu | Glu | Lys | Gln | Gly | |
| | | 225 | | | | | 230 | | | | | 235 | | | | |
| GTC | TCC | AAG | AGA | CAT | GTT | AGG | ATA | AGC | AGG | TCT | TTG | CAC | CAA | GAT | GAA | 770 |
| Val | Ser | Lys | Arg | His | Val | Arg | Ile | Ser | Arg | Ser | Leu | His | Gln | Asp | Glu | |
| | 240 | | | | | 245 | | | | | 250 | | | | | |
| CAC | AGC | TGG | TCA | CAG | ATA | AGG | CCA | TTG | CTA | GTA | ACT | TTT | GGC | CAT | GAT | 818 |
| His | Ser | Trp | Ser | Gln | Ile | Arg | Pro | Leu | Leu | Val | Thr | Phe | Gly | His | Asp | |
| 255 | | | | | 260 | | | | | 265 | | | | | 270 | |
| GGA | AAA | GGG | CAT | CCT | CTC | CAC | AAA | AGA | GAA | AAA | CGT | CAA | GCC | AAA | CAC | 866 |
| Gly | Lys | Gly | His | Pro | Leu | His | Lys | Arg | Glu | Lys | Arg | Gln | Ala | Lys | His | |
| | | | | 275 | | | | | 280 | | | | | 285 | | |
| AAA | CAG | CGG | AAA | CGC | CTT | AAG | TCC | AGC | TGT | AAG | AGA | CAC | CCT | TTG | TAC | 914 |
| Lys | Gln | Arg | Lys | Arg | Leu | Lys | Ser | Ser | Cys | Lys | Arg | His | Pro | Leu | Tyr | |
| | | | 290 | | | | | 295 | | | | | 300 | | | |
| GTG | GAC | TTC | AGT | GAC | GTG | GGG | TGG | AAT | GAC | TGG | ATT | GTG | GCT | CCC | CCG | 962 |
| Val | Asp | Phe | Ser | Asp | Val | Gly | Trp | Asn | Asp | Trp | Ile | Val | Ala | Pro | Pro | |
| | | 305 | | | | | 310 | | | | | 315 | | | | |
| GGG | TAT | CAC | GCC | TTT | TAC | TGC | CAC | GGA | GAA | TGC | CCT | TTT | CCT | CTG | GCT | 1010 |
| Gly | Tyr | His | Ala | Phe | Tyr | Cys | His | Gly | Glu | Cys | Pro | Phe | Pro | Leu | Ala | |
| | 320 | | | | | 325 | | | | | 330 | | | | | |
| GAT | CAT | CTG | AAC | TCC | ACT | AAT | CAT | GCC | ATT | GTT | CAG | ACG | TTG | GTC | AAC | 1058 |
| Asp | His | Leu | Asn | Ser | Thr | Asn | His | Ala | Ile | Val | Gln | Thr | Leu | Val | Asn | |
| 335 | | | | | 340 | | | | | 345 | | | | | 350 | |
| TCT | GTT | AAC | TCT | AAG | ATT | CCT | AAG | GCA | TGC | TGT | GTC | CCG | ACA | GAA | CTC | 1106 |
| Ser | Val | Asn | Ser | Lys | Ile | Pro | Lys | Ala | Cys | Cys | Val | Pro | Thr | Glu | Leu | |
| | | | | 355 | | | | | 360 | | | | | 365 | | |
| AGT | GCT | ATC | TCG | ATG | CTG | TAC | CTT | GAC | GAG | AAT | GAA | AAG | GTT | GTA | TTA | 1154 |
| Ser | Ala | Ile | Ser | Met | Leu | Tyr | Leu | Asp | Glu | Asn | Glu | Lys | Val | Val | Leu | |
| | | | 370 | | | | | 375 | | | | | 380 | | | |
| AAG | AAC | TAT | CAG | GAT | ATG | GTT | GTG | GAG | GGT | TGT | GGG | TGT | CGC | | | 1196 |
| Lys | Asn | Tyr | Gln | Asp | Met | Val | Val | Glu | Gly | Cys | Gly | Cys | Arg | | | |
| | | 385 | | | | | 390 | | | | | 395 | | | | |

TAGTACAGCA AAATTAAATA CATAAATATA TATATATATA TATATTTTAG AAAAAAGAAA     1256

AAAA     1260

( 2 ) INFORMATION FOR SEQ ID NO:15:

( i ) SEQUENCE CHARACTERISTICS:
        ( A ) LENGTH: 396 amino acids
        ( B ) TYPE: amino acid (D) TOPOLOGY: linear (ii) MOLECULE TYPE: protein (xi) SEQUENCE DESCRIPTION: SEQ ID NO:15:

| Met | Val | Ala | Gly | Thr | Arg | Cys | Leu | Leu | Ala | Leu | Leu | Leu | Pro | Gln | Val |
|---|---|---|---|---|---|---|---|---|---|---|---|---|---|---|---|
| 1 | | | | 5 | | | | | 10 | | | | | 15 | |

| Leu | Leu | Gly | Gly | Ala | Ala | Gly | Leu | Val | Pro | Glu | Leu | Gly | Arg | Arg | Lys |
|---|---|---|---|---|---|---|---|---|---|---|---|---|---|---|---|
| | | | 20 | | | | | 25 | | | | | 30 | | |

| Phe | Ala | Ala | Ala | Ser | Ser | Gly | Arg | Pro | Ser | Ser | Gln | Pro | Ser | Asp | Glu |
|---|---|---|---|---|---|---|---|---|---|---|---|---|---|---|---|
| | | 35 | | | | | 40 | | | | 45 | | | | |

| Val | Leu | Ser | Glu | Phe | Glu | Leu | Arg | Leu | Leu | Ser | Met | Phe | Gly | Leu | Lys |
|---|---|---|---|---|---|---|---|---|---|---|---|---|---|---|---|
| | 50 | | | | | 55 | | | | | 60 | | | | |

| Gln | Arg | Pro | Thr | Pro | Ser | Arg | Asp | Ala | Val | Pro | Pro | Tyr | Met | Leu |
|---|---|---|---|---|---|---|---|---|---|---|---|---|---|---|
| 65 | | | | | 70 | | | | 75 | | | | | 80 |

| Asp | Leu | Tyr | Arg | Arg | His | Ser | Gly | Gln | Pro | Gly | Ser | Pro | Ala | Pro | Asp |
|---|---|---|---|---|---|---|---|---|---|---|---|---|---|---|---|
| | | | | 85 | | | | | 90 | | | | | 95 | |

| His | Arg | Leu | Glu | Arg | Ala | Ala | Ser | Arg | Ala | Asn | Thr | Val | Arg | Ser | Phe |
|---|---|---|---|---|---|---|---|---|---|---|---|---|---|---|---|
| | | | | 100 | | | | | 105 | | | | | 110 | |

| His | His | Glu | Glu | Ser | Leu | Glu | Glu | Leu | Pro | Glu | Thr | Ser | Gly | Lys | Thr |
|---|---|---|---|---|---|---|---|---|---|---|---|---|---|---|---|
| | | | 115 | | | | | 120 | | | | | 125 | | |

| Thr | Arg | Arg | Phe | Phe | Phe | Asn | Leu | Ser | Ser | Ile | Pro | Thr | Glu | Glu | Phe |
|---|---|---|---|---|---|---|---|---|---|---|---|---|---|---|---|
| | | 130 | | | | | 135 | | | | 140 | | | | |

| Ile | Thr | Ser | Ala | Glu | Leu | Gln | Val | Phe | Arg | Glu | Gln | Met | Gln | Asp | Ala |
|---|---|---|---|---|---|---|---|---|---|---|---|---|---|---|---|
| 145 | | | | | 150 | | | | | 155 | | | | | 160 |

| Leu | Gly | Asn | Asn | Ser | Ser | Phe | His | His | Arg | Ile | Asn | Ile | Tyr | Glu | Ile |
|---|---|---|---|---|---|---|---|---|---|---|---|---|---|---|---|
| | | | | 165 | | | | | 170 | | | | | 175 | |

| Ile | Lys | Pro | Ala | Thr | Ala | Asn | Ser | Lys | Phe | Pro | Val | Thr | Ser | Leu | Leu |
|---|---|---|---|---|---|---|---|---|---|---|---|---|---|---|---|
| | | | 180 | | | | | 185 | | | | | 190 | | |

| Asp | Thr | Arg | Leu | Val | Asn | Gln | Asn | Ala | Ser | Arg | Trp | Glu | Ser | Phe | Asp |
|---|---|---|---|---|---|---|---|---|---|---|---|---|---|---|---|
| | | 195 | | | | | 200 | | | | | 205 | | | |

| Val | Thr | Pro | Ala | Val | Met | Arg | Trp | Thr | Ala | Gln | Gly | His | Ala | Asn | His |
|---|---|---|---|---|---|---|---|---|---|---|---|---|---|---|---|
| | 210 | | | | | 215 | | | | | 220 | | | | |

| Gly | Phe | Val | Val | Glu | Val | Ala | His | Leu | Glu | Glu | Lys | Gln | Gly | Val | Ser |
|---|---|---|---|---|---|---|---|---|---|---|---|---|---|---|---|
| 225 | | | | | 230 | | | | | 235 | | | | | 240 |

| Lys | Arg | His | Val | Arg | Ile | Ser | Arg | Ser | Leu | His | Gln | Asp | Glu | His | Ser |
|---|---|---|---|---|---|---|---|---|---|---|---|---|---|---|---|
| | | | | 245 | | | | | 250 | | | | | 255 | |

| Trp | Ser | Gln | Ile | Arg | Pro | Leu | Leu | Val | Thr | Phe | Gly | His | Asp | Gly | Lys |
|---|---|---|---|---|---|---|---|---|---|---|---|---|---|---|---|
| | | | 260 | | | | | 265 | | | | | 270 | | |

| Gly | His | Pro | Leu | His | Lys | Arg | Glu | Lys | Arg | Gln | Ala | Lys | His | Lys | Gln |
|---|---|---|---|---|---|---|---|---|---|---|---|---|---|---|---|
| | | 275 | | | | | 280 | | | | | 285 | | | |

| Arg | Lys | Arg | Leu | Lys | Ser | Ser | Cys | Lys | Arg | His | Pro | Leu | Tyr | Val | Asp |
|---|---|---|---|---|---|---|---|---|---|---|---|---|---|---|---|
| | 290 | | | | | 295 | | | | | 300 | | | | |

| Phe | Ser | Asp | Val | Gly | Trp | Asn | Asp | Trp | Ile | Val | Ala | Pro | Pro | Gly | Tyr |
|---|---|---|---|---|---|---|---|---|---|---|---|---|---|---|---|
| 305 | | | | | 310 | | | | | 315 | | | | | 320 |

| His | Ala | Phe | Tyr | Cys | His | Gly | Glu | Cys | Pro | Phe | Pro | Leu | Ala | Asp | His |
|---|---|---|---|---|---|---|---|---|---|---|---|---|---|---|---|
| | | | | 325 | | | | | 330 | | | | | 335 | |

| Leu | Asn | Ser | Thr | Asn | His | Ala | Ile | Val | Gln | Thr | Leu | Val | Asn | Ser | Val |
|---|---|---|---|---|---|---|---|---|---|---|---|---|---|---|---|
| | | | 340 | | | | | 345 | | | | | 350 | | |

| Asn | Ser | Lys | Ile | Pro | Lys | Ala | Cys | Cys | Val | Pro | Thr | Glu | Leu | Ser | Ala |
|---|---|---|---|---|---|---|---|---|---|---|---|---|---|---|---|
| | | 355 | | | | | 360 | | | | | 365 | | | |

| Ile | Ser | Met | Leu | Tyr | Leu | Asp | Glu | Asn | Glu | Lys | Val | Val | Leu | Lys | Asn |
|---|---|---|---|---|---|---|---|---|---|---|---|---|---|---|---|
| | 370 | | | | | 375 | | | | | 380 | | | | |

| Tyr | Gln | Asp | Met | Val | Val | Glu | Gly | Cys | Gly | Cys | Arg |
|---|---|---|---|---|---|---|---|---|---|---|---|
| 385 | | | | | 390 | | | | | 395 | |

( 2 ) INFORMATION FOR SEQ ID NO:16:

( i ) SEQUENCE CHARACTERISTICS:
        ( A ) LENGTH: 574 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: HOMO SAPIENS ( i x ) FEATURE:
        ( A ) NAME/KEY: CDS
        ( B ) LOCATION: 1..327
        ( D ) OTHER INFORMATION: /product="MATURE hBMP3 (PARTIAL)"
        / note="THIS PARTIAL SEQUENCE OF THE MATURE HUMAN
        BMP3 PROTEIN INCLUDE THE FIRST THREE CYSTEINES OF
        THE CONSERVED 7 CYSTEINE SKELETON. SEE US PAT. NO.
        5,011,691 FOR 102 C-TERMINAL SEQUENCE (CBMP3)."

( i x ) FEATURE:
        ( A ) NAME/KEY: intron
        ( B ) LOCATION: 328..574

( x i ) SEQUENCE DESCRIPTION: SEQ ID NO:16:

```
CGA GCT TCT AAA ATA GAA TAC CAG TAT AAA AAG GAT GAG GTG TGG GAG      48
Arg Ala Ser Lys Ile Glu Tyr Gln Tyr Lys Lys Asp Glu Val Trp Glu
 1               5                  10                  15

GAG AGA AAG CCT TAC AAG ACC CTT CAG GGC TCA GGC CCT GAA AAG AGT      96
Glu Arg Lys Pro Tyr Lys Thr Leu Gln Gly Ser Gly Pro Glu Lys Ser
            20                  25                  30

AAG AAT AAA AAG AAA CAG AGA AAG GGG CCT CAT CGG AAG AGC CAG ACG     144
Lys Asn Lys Lys Lys Gln Arg Lys Gly Pro His Arg Lys Ser Gln Thr
        35                  40                  45

CTC CAA TTT GAT GAG CAG ACC CTG AAA AAG GCA AGG AGA AAG CAG TGG     192
Leu Gln Phe Asp Glu Gln Thr Leu Lys Lys Ala Arg Arg Lys Gln Trp
    50                  55                  60

ATT GAA CCT CGG AAT TGC GCC AGG AGA TAC CTC AAG GTA GAC TTT GCA     240
Ile Glu Pro Arg Asn Cys Ala Arg Arg Tyr Leu Lys Val Asp Phe Ala
65                  70                  75                  80

GAT ATT GGC TGG AGT GAA TGG ATT ATC TCC CCC AAG TCC TTT GAT GCC     288
Asp Ile Gly Trp Ser Glu Trp Ile Ile Ser Pro Lys Ser Phe Asp Ala
                85                  90                  95

TAT TAT TGC TCT GGA GCA TGC CAG TTC CCC ATG CCA AAG GTAGCCATTG      337
Tyr Tyr Cys Ser Gly Ala Cys Gln Phe Pro Met Pro Lys
                100                 105

TTCTCTGTCC TGTACTTACT TCCTATTTCC ATTAGTAGAA AGACACATTG ACTAAGTTAG   397

TGTGCATATA GGGGGTTTGT GTAAGTGTTT GTGTTTCCAT TTGCAAAATC CATTGGGACC   457

CTTATTTACT ACATTCTAAA CCATAATAGG TAATATGGTT ATTCTTGGTT TCTCTTTAAT   517

GGTTGTTAAA GTCATATGAA GTCAGTATTG GTATAAAGAA GGATATGAGA AAAAAA       574
```

( 2 ) INFORMATION FOR SEQ ID NO:17:

( i ) SEQUENCE CHARACTERISTICS:
        ( A ) LENGTH: 109 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Arg Ala Ser Lys Ile Glu Tyr Gln Tyr Lys Lys Asp Glu Val Trp Glu
 1               5                  10                  15

Glu Arg Lys Pro Tyr Lys Thr Leu Gln Gly Ser Gly Pro Glu Lys Ser
            20                  25                  30
```

```
Lys Asn Lys Lys Lys Gln Arg Lys Gly Pro His Arg Lys Ser Gln Thr
     35              40                  45

Leu Gln Phe Asp Glu Gln Thr Leu Lys Lys Ala Arg Arg Lys Gln Trp
     50              55                  60

Ile Glu Pro Arg Asn Cys Ala Arg Arg Tyr Leu Lys Val Asp Phe Ala
 65              70                  75                      80

Asp Ile Gly Trp Ser Glu Trp Ile Ile Ser Pro Lys Ser Phe Asp Ala
             85                  90                  95

Tyr Tyr Cys Ser Gly Ala Cys Gln Phe Pro Met Pro Lys
             100                 105
```

( 2 ) INFORMATION FOR SEQ ID NO:18:

( i ) SEQUENCE CHARACTERISTICS:
        ( A ) LENGTH: 1788 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: HOMO SAPIENS
        ( F ) TISSUE TYPE: HIPPOCAMPUS ( i x ) FEATURE:
        ( A ) NAME/KEY: CDS
        ( B ) LOCATION: 403..1626
        ( C ) IDENTIFICATION METHOD: experimental
        ( D ) OTHER INFORMATION: /function="OSTEOGENIC PROTEIN"
            / product="BMP2B"
            / evidence=EXPERIMENTAL
            / note="BMP2B (CDNA)"

( x i ) SEQUENCE DESCRIPTION: SEQ ID NO:18:

```
GAATTCGGGG CAGAGGAGGA GGGAGGGAGG GAAGGAGCGC GGAGCCCGGC CCGGAAGCTA        60

GGTGAGTGTG GCATCCGAGC TGAGGGACGC GAGCCTGAGA CGCCGCTGCT GCTCCGGCTG       120

AGTATCTAGC TTGTCTCCCC GATGGGATTC CCGTCCAAGC TATCTCGAGC CTGCAGCGCC       180

ACAGTCCCCG GCCCTCGCCC AGGTTCACTG CAACCGTTCA GAGGTCCCCA GGAGCTGCTG       240

CTGGCGAGCC CGCTACTGCA GGGACCTATG GAGCCATTCC GTAGTGCCAT CCCGAGCAAC       300

GCACTGCTGC AGCTTCCCTG AGCCTTTCCA GCAAGTTTGT TCAAGATTGG CTGTCAAGAA       360

TCATGGACTG TTATTATATG CCTTGTTTTC TGTCAAGACA CC ATG ATT CCT GGT         414
                                                Met Ile Pro Gly
                                                 1

AAC CGA ATG CTG ATG GTC GTT TTA TTA TGC CAA GTC CTG CTA GGA GGC         462
Asn Arg Met Leu Met Val Val Leu Leu Cys Gln Val Leu Leu Gly Gly
  5              10                  15                  20

GCG AGC CAT GCT AGT TTG ATA CCT GAG ACG GGG AAG AAA AAA GTC GCC         510
Ala Ser His Ala Ser Leu Ile Pro Glu Thr Gly Lys Lys Lys Val Ala
                  25                  30                  35

GAG ATT CAG GGC CAC GCG GGA GGA CGC CGC TCA GGG CAG AGC CAT GAG         558
Glu Ile Gln Gly His Ala Gly Gly Arg Arg Ser Gly Gln Ser His Glu
             40                  45                  50

CTC CTG CGG GAC TTC GAG GCG ACA CTT CTG CAG ATG TTT GGG CTG CGC         606
Leu Leu Arg Asp Phe Glu Ala Thr Leu Leu Gln Met Phe Gly Leu Arg
         55                  60                  65

CGC CGC CCG CAG CCT AGC AAG AGT GCC GTC ATT CCG GAC TAC ATG CGG         654
Arg Arg Pro Gln Pro Ser Lys Ser Ala Val Ile Pro Asp Tyr Met Arg
     70                  75                  80

GAT CTT TAC CGG CTT CAG TCT GGG GAG GAG GAG GAA GAG CAG ATC CAC         702
```

```
Asp Leu Tyr Arg Leu Gln Ser Gly Glu Glu Glu Glu Gln Ile His
 85              90              95             100

AGC ACT GGT CTT GAG TAT CCT GAG CGC CCG GCC AGC CGG GCC AAC ACC    750
Ser Thr Gly Leu Glu Tyr Pro Glu Arg Pro Ala Ser Arg Ala Asn Thr
             105              110              115

GTG AGG AGC TTC CAC CAC GAA GAA CAT CTG GAG AAC ATC CCA GGG ACC    798
Val Arg Ser Phe His His Glu Glu His Leu Glu Asn Ile Pro Gly Thr
             120              125              130

AGT GAA AAC TCT GCT TTT CGT TTC CTC TTT AAC CTC AGC AGC ATC CCT    846
Ser Glu Asn Ser Ala Phe Arg Phe Leu Phe Asn Leu Ser Ser Ile Pro
         135              140              145

GAG AAC GAG GTG ATC TCC TCT GCA GAG CTT CGG CTC TTC CGG GAG CAG    894
Glu Asn Glu Val Ile Ser Ser Ala Glu Leu Arg Leu Phe Arg Glu Gln
         150              155              160

GTG GAC CAG GGC CCT GAT TGG GAA AGG GGC TTC CAC CGT ATA AAC ATT    942
Val Asp Gln Gly Pro Asp Trp Glu Arg Gly Phe His Arg Ile Asn Ile
165              170              175              180

TAT GAG GTT ATG AAG CCC CCA GCA GAA GTG GTG CCT GGG CAC CTC ATC    990
Tyr Glu Val Met Lys Pro Pro Ala Glu Val Val Pro Gly His Leu Ile
             185              190              195

ACA CGA CTA CTG GAC ACG AGA CTG GTC CAC CAC AAT GTG ACA CGG TGG   1038
Thr Arg Leu Leu Asp Thr Arg Leu Val His His Asn Val Thr Arg Trp
             200              205              210

GAA ACT TTT GAT GTG AGC CCT GCG GTC CTT CGC TGG ACC CGG GAG AAG   1086
Glu Thr Phe Asp Val Ser Pro Ala Val Leu Arg Trp Thr Arg Glu Lys
             215              220              225

CAG CCA AAC TAT GGG CTA GCC ATT GAG GTG ACT CAC CTC CAT CAG ACT   1134
Gln Pro Asn Tyr Gly Leu Ala Ile Glu Val Thr His Leu His Gln Thr
         230              235              240

CGG ACC CAC CAG GGC CAG CAT GTC AGG ATT AGC CGA TCG TTA CCT CAA   1182
Arg Thr His Gln Gly Gln His Val Arg Ile Ser Arg Ser Leu Pro Gln
245              250              255              260

GGG AGT GGG AAT TGG GCC CAG CTC CGG CCC CTC CTG GTC ACC TTT GGC   1230
Gly Ser Gly Asn Trp Ala Gln Leu Arg Pro Leu Leu Val Thr Phe Gly
             265              270              275

CAT GAT GGC CGG GGC CAT GCC TTG ACC CGA CGC CGG AGG GCC AAG CGT   1278
His Asp Gly Arg Gly His Ala Leu Thr Arg Arg Arg Arg Ala Lys Arg
             280              285              290

AGC CCT AAG CAT CAC TCA CAG CGG GCC AGG AAG AAG AAT AAG AAC TGC   1326
Ser Pro Lys His His Ser Gln Arg Ala Arg Lys Lys Asn Lys Asn Cys
         295              300              305

CGG CGC CAC TCG CTC TAT GTG GAC TTC AGC GAT GTG GGC TGG AAT GAC   1374
Arg Arg His Ser Leu Tyr Val Asp Phe Ser Asp Val Gly Trp Asn Asp
         310              315              320

TGG ATT GTG GCC CCA CCA GGC TAC CAG GCC TTC TAC TGC CAT GGG GAC   1422
Trp Ile Val Ala Pro Pro Gly Tyr Gln Ala Phe Tyr Cys His Gly Asp
325              330              335              340

TGC CCC TTT CCA CTG GCT GAC CAC CTC AAC TCA ACC AAC CAT GCC ATT   1470
Cys Pro Phe Pro Leu Ala Asp His Leu Asn Ser Thr Asn His Ala Ile
             345              350              355

GTG CAG ACC CTG GTC AAT TCT GTC AAT TCC AGT ATC CCC AAA GCC TGT   1518
Val Gln Thr Leu Val Asn Ser Val Asn Ser Ser Ile Pro Lys Ala Cys
             360              365              370

TGT GTG CCC ACT GAA CTG AGT GCC ATC TCC ATG CTG TAC CTG GAT GAG   1566
Cys Val Pro Thr Glu Leu Ser Ala Ile Ser Met Leu Tyr Leu Asp Glu
             375              380              385

TAT GAT AAG GTG GTA CTG AAA AAT TAT CAG GAG ATG GTA GTA GAG GGA   1614
Tyr Asp Lys Val Val Leu Lys Asn Tyr Gln Glu Met Val Val Glu Gly
             390              395              400

TGT GGG TGC CGC TGAGATCAGG CAGTCCTTGA GGATAGACAG ATATACACAC       1666
Cys Gly Cys Arg
405
```

```
ACACACACAC ACACCACATA CACCACACAC ACACGTTCCC ATCCACTCAC CCACACACTA      1726

CACAGACTGC TTCCTTATAG CTGGACTTTT ATTTAAAAAA AAAAAAAAAA AAACCCGAAT      1786

TC                                                                     1788
```

( 2 ) INFORMATION FOR SEQ ID NO:19:

( i ) SEQUENCE CHARACTERISTICS:
        ( A ) LENGTH: 408 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

```
Met Ile Pro Gly Asn Arg Met Leu Met Val Val Leu Leu Cys Gln Val
 1               5                  10                  15

Leu Leu Gly Gly Ala Ser His Ala Ser Leu Ile Pro Glu Thr Gly Lys
                20                  25                  30

Lys Lys Val Ala Glu Ile Gln Gly His Ala Gly Gly Arg Arg Ser Gly
            35                  40                  45

Gln Ser His Glu Leu Leu Arg Asp Phe Glu Ala Thr Leu Leu Gln Met
        50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Gln Ile His Ser Thr Gly Leu Glu Tyr Pro Glu Arg Pro Ala Ser
                100                 105                 110

Arg Ala Asn Thr Val Arg Ser Phe His His Glu Glu His Leu Glu Asn
            115                 120                 125

Ile Pro Gly Thr Ser Glu Asn Ser Ala Phe Arg Phe Leu Phe Asn Leu
        130                 135                 140

Ser Ser Ile Pro Glu Asn Glu Val Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
                180                 185                 190

Gly His Leu Ile Thr Arg Leu Leu Asp Thr Arg Leu Val His His Asn
            195                 200                 205

Val Thr Arg Trp Glu Thr Phe Asp Val Ser Pro Ala Val Leu Arg Trp
        210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
                260                 265                 270

Val Thr Phe Gly His Asp Gly Arg Gly His Ala Leu Thr Arg Arg Arg
            275                 280                 285

Arg Ala Lys Arg Ser Pro Lys His His Ser Gln Arg Ala Arg Lys Lys
        290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335
```

-continued

```
Cys His Gly Asp Cys Pro Phe Pro Leu Ala Asp His Leu Asn Ser Thr
         340                 345                 350

Asn His Ala Ile Val Gln Thr Leu Val Asn Ser Val Asn Ser Ser Ile
         355                 360                 365

Pro Lys Ala Cys Cys Val Pro Thr Glu Leu Ser Ala Ile Ser Met Leu
370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405
```

( 2 ) INFORMATION FOR SEQ ID NO:20:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: HOMO SAPIENS ( i x ) FEATURE:
        ( A ) NAME/KEY: Protein
        ( B ) LOCATION: 1..102
        ( D ) OTHER INFORMATION: /note="BMP5"

( x i ) SEQUENCE DESCRIPTION: SEQ ID NO:20:

```
Cys Lys Lys His Glu Leu Tyr Val Ser Phe Arg Asp Leu Gly Trp Gln
1               5                   10                  15

Asp Trp Ile Ile Ala Pro Glu Gly Tyr Ala Ala Phe Tyr Cys Asp Gly
                20                  25                  30

Glu Cys Ser Phe Pro Leu Asn Ala His Met Asn Ala Thr Asn His Ala
            35                  40                  45

Ile Val Gln Thr Leu Val His Leu Met Phe Pro Asp His Val Pro Lys
        50                  55                  60

Pro Cys Cys Ala Pro Thr Lys Leu Asn Ala Ile Ser Val Leu Tyr Phe
65                  70                  75                  80

Asp Asp Ser Ser Asn Val Ile Leu Lys Lys Tyr Arg Asn Met Val Val
                85                  90                  95

Arg Ser Cys Gly Cys His
            100
```

( 2 ) INFORMATION FOR SEQ ID NO:21:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: HOMO SAPIENS ( i x ) FEATURE:
        ( A ) NAME/KEY: Protein
        ( B ) LOCATION: 1..102
        ( D ) OTHER INFORMATION: /note="BMP6"

( x i ) SEQUENCE DESCRIPTION: SEQ ID NO:21:

```
Cys Arg Lys His Glu Leu Tyr Val Ser Phe Gln Asp Leu Gly Trp Gln
1               5                   10                  15

Asp Trp Ile Ile Ala Pro Lys Gly Tyr Ala Ala Asn Tyr Cys Asp Gly
```

-continued

```
                    20                          25                          30

Glu  Cys  Ser  Phe  Pro  Leu  Asn  Ala  His  Met  Asn  Ala  Thr  Asn  His  Ala
                  35                      40                      45

Ile  Val  Gln  Thr  Leu  Val  His  Leu  Met  Asn  Pro  Glu  Tyr  Val  Pro  Lys
             50                      55                      60

Pro  Cys  Cys  Ala  Pro  Thr  Lys  Leu  Asn  Ala  Ile  Ser  Val  Leu  Tyr  Phe
        65                      70                      75                      80

Asp  Asp  Asn  Ser  Asn  Val  Ile  Leu  Lys  Lys  Tyr  Arg  Trp  Met  Val  Val
                            85                      90                      95

Arg  Ala  Cys  Gly  Cys  His
                       100
```

(2) INFORMATION FOR SEQ ID NO:22:

(i) SEQUENCE CHARACTERISTICS:
        (A) LENGTH: 102 amino acids
        (B) TYPE: amino acid
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label=OPX
        / note="WHEREIN XAA AT EACH POS'N IS INDEPENDENTLY
        SELECTED FROM THE RESIDUES OCCURRING AT THE CORRESPONDING
        POS'N IN THE C TERMINAL SEQUENCE OF MOUSE OR HUMAN OP1
        OR OP2 (SEE SEQ. ID NOS.1,8,10 AND 12.)"

(xi) SEQUENCE DESCRIPTION: SEQ ID NO:22:

```
        Cys  Xaa  Xaa  His  Glu  Leu  Tyr  Val  Xaa  Phe  Xaa  Asp  Leu  Gly  Trp  Xaa
        1                      5                      10                      15

Asp  Trp  Xaa  Ile  Ala  Pro  Xaa  Gly  Tyr  Xaa  Ala  Tyr  Tyr  Cys  Glu  Gly
                       20                      25                      30

Glu  Cys  Xaa  Phe  Pro  Leu  Xaa  Ser  Xaa  Met  Asn  Ala  Thr  Asn  His  Ala
                  35                      40                      45

Ile  Xaa  Gln  Xaa  Leu  Val  His  Xaa  Xaa  Xaa  Pro  Xaa  Xaa  Val  Pro  Lys
             50                      55                      60

Xaa  Cys  Cys  Ala  Pro  Thr  Xaa  Leu  Xaa  Ala  Xaa  Ser  Val  Leu  Tyr  Xaa
        65                      70                      75                      80

Asp  Xaa  Ser  Xaa  Asn  Val  Xaa  Leu  Xaa  Lys  Xaa  Arg  Asn  Met  Val  Val
                            85                      90                      95

Xaa  Ala  Cys  Gly  Cys  His
                       100
```

PROSTHETIC DEVICES HAVING ENHANCED OSTEOGENIC PROPERTIES

REFERENCE TO RELATED APPLICATIONS

This application is a continuation-in-part of copending U.S. application Ser. No. 07/841,646, filed Feb. 21, 1992, now U.S. Pat. No. 5,266,683 which is a continuation-in-part of U.S. application Ser. Nos. : 1) 07/827,052, filed Jan. 28, 1992, now U.S. Pat. No. 5,250,302, which is a divisional of U.S. Ser. No. 07/179,406, filed Apr. 8, 1988, now U.S. Pat. No. 4,968,590; 2) 07/579,865, filed Sep. 7, 1990, now U.S. Pat. No. 5,108,753, a divisional of U.S. Ser. No. 07/179,406; 3) 07/621,849, filed Dec. 4, 1990, now abandoned, a divisional of U.S. Ser. No. 07/232,630, filed Aug. 15, 1988, now abandoned, that was a continuation-in-part of 07/179,406; 4) 07/621,988, filed Dec. 4, 1990, and now abandoned, a divisional of 07/315,342 filed Feb. 23, 1989, now U.S. Pat. No. 5,011,691 and which is a continuation-in-part of 07/232,630; 5) 07/810,560, filed Dec. 20, 1991, now abandoned, a continuation of 07/660,162, filed Feb. 22, 1991, now abandoned, that was a continuation of 07/422,699, filed Oct. 17, 1989, now abandoned, that was a continuation-in-part of 07/315,342; 6) 07/569,920, filed Aug. 20, 1990, now abandoned, that was a continuation-in-part of 07/422,699 and 07/483,913, which is continuation-in-part of 07/422,613, filed Oct. 17, 1989, now U.S. Pat. No. 4,975,526 and which is a continuation-in-part of 07/315,342; 7) 07/600,024, filed Oct. 18, 1990, now abandoned, a continuation-in-part of 07/569,920; 8) 07/599,543, filed Oct. 18, 1990, now abandoned, a continuation-in-part of 07/569,920; 9) 07/616,374, filed Nov. 21, 1990, now U.S. Pat. No. 5,162,114 a divisional of 07/422,613; and 10) 07/483,913, filed Feb. 22, 1990, now U.S. Pat. No. 5,171,574.

BACKGROUND OF THE INVENTION

Regeneration of skeletal tissues is thought to be regulated by specific protein factors that are naturally present within bone matrix. When a bone is damaged, these factors stimulate cells to form new cartilage and bone tissue which replaces or repairs lost or damaged bone. Regeneration of bone is particularly important where prosthetic implants are used without bonding cement to replace diseased bone, as in hip replacement. In these cases, formation of a tight bond between the prosthesis and the existing bone is very important, and successful function depends on the interaction between the implant and the bone tissue at the interface.

Bone healing can be stimulated by one or more osteogenic proteins which can induce a developmental cascade of cellular events resulting in endochondral bone formation. Proteins stimulating bone growth have been referred to in the literature as bone morphogenic proteins, bone inductive proteins, osteogenic proteins, osteogenin or osteoinductive proteins.

U.S. Pat. No. 4,968,590 (Nov. 6, 1990) discloses the purification of "substantially pure" osteogenic protein from bone, capable of inducing endochondral bone formation in a mammal when implanted in the mammal in association with a matrix, and having a half maximum activity of at least about 25 to 50 nanograms per 25 milligrams of implanted matrix. Higher activity subsequently has been shown for this protein, e.g., 0.8-1.0 ng of osteogenic protein per mg of implant matrix, as disclosed in U.S. Pat. No. 5,011,691. This patent also disclosed a consensus DNA sequence probe useful for identifying genes encoding osteogenic proteins, and a number of human genes encoding osteogenic proteins identified using the consensus probe, including a previously unidentified gene referred to therein as "OP1" (osteogenic protein-1). The consensus probe also identified DNA sequences corresponding to sequences termed BMP-2 Class I and Class II ("BMP2" and "BMP4" respectively) and BMP3 in International Appl. No. PCT/US87/01537. The osteogenic proteins encoded by these sequences are referred to herein as "CBMP2A," "CBMP2B", and "CBMP3", respectively. U.S. Pat. No. 5,011,691 also defined a consensus "active region" required for osteogenic activity and described several novel biosynthetic constructs using this consensus sequence which were capable of inducing cartilage or bone formation in a mammal in association with a matrix.

These and other researchers have stated that successful implantation of the osteogenic factors for endochondral bone formation requires that the proteins be associated with a suitable carrier material or matrix which maintains the proteins at the site of application. Bone collagen particles which remain after demineralization, guanidine extraction and delipidation of pulverized bone have been used for this purpose. Many osteoinductive proteins are useful cross-species. However, demineralized, delipidated, guanidine-extracted xenogenic collagen matrices typically have inhibited bone induction in vivo. Sampath and Reddi (1983) *Proc. Natl. Acad. Sci. USA*, 80: 6591-6594. Recently, however, Sampath et al. have described a method for treating demineralized guanidine-extracted bone powder to create a matrix useful for xenogenic implants. See, U.S. Pat. No. 4,975,526 (Dec. 4, 1990). Other useful matrix materials include for example, collagen; homopolymers or copolymers of glycolic acid, lactic acid, and butryic acid, including derivatives thereof; and ceramics, such as hydroxyapatite, tricalcium phosphate and other calcium phosphates. Combinations of these matrix materials also may be useful.

Orthopedic implants have traditionally been attached to natural bone using bone cement. More recently, cementless prostheses have been used, in which the portion of the prosthesis that contacts the natural bone is coated with a porous material. M. Spector, *J. Arthroplasty*, 2(2):163-176 (1987); and Cook et al., *Clin. Orthoped. and Rel. Res.*, 232: 225-243 (1988). Cementless fixation is preferred because biological fixation of the prosthesis is stronger when osseointegration is achieved. The porous coatings reportedly stimulate bone ingrowth resulting in enhanced biological fixation of the prosthesis. However, there are several problems with porous-coated prostheses. For example, careful prosthetic selection is required to obtain a close fit with the bone to ensure initial mechanical stabilization of the device, and surgical precision is required to ensure initial implant-bone contact to promote bone ingrowth. Porous coated implants have not resulted in bone ingrowth in some instances, for example, in porous coated tibial plateaus used in knee replacements. A prosthetic implant that results in significant bone ingrowth and forms a strong bond with the natural bone at the site of the join would be very valuable.

The current state of the art for the anchoring of embedded implants such as dental implants also is unsatisfactory. Typically, dental implant fixation first requires preparing a tooth socket in the jawbone of an individual for prosthesis implantation by allowing bone ingrowth into the socket void to fill in the socket. This preparatory step alone can take several months to complete. The prosthesis then is threaded into the new bone in the socket and new bone is allowed to regrow around the threaded portion of the implant embedded in the socket. The interval between tooth extraction and prosthetic restoration therefore can take up to eight months. In addition, threading the prosthesis into bone can damage the integrity of the bone. Prosthetic dental implants that can improve osseointegration and reduce the time and effort for fixation would be advantageous.

SUMMARY OF THE INVENTION

The present invention relates to a method of enhancing the growth of bone at the site of implantation of a prosthesis to form a bond between the prosthesis and the existing bone. As used herein, a prosthesis is understood to describe the addition of an artificial part to supply a defect in the body. The method involves coating or otherwise contacting all or a portion of the prosthesis that will be in contact with bone with a substantially pure osteogenic protein. The prosthesis first may be coated with the osteogenic protein and then implanted in the individual at a site wherein the bone tissue and the surface of the prosthesis are maintained in close proximity for a time sufficient to permit enhanced bone tissue growth between the tissue and the implanted prosthesis. Alternatively, the site of implantation first may be treated with substantially pure osteogenic protein and the prosthesis then implanted at the treated site such that all or a portion of the prosthesis is in contact with the osteogenic protein at the site, and the prosthesis, the osteogenic protein and the existing bone tissue are maintained in close proximity to one another for a time sufficient to permit enhanced bone tissue growth between the tissue and the prosthesis. The osteogenic protein associated with the implanted prosthesis stimulates bone growth around the prosthesis and causes a stronger bond to form between the prosthesis and the existing bone than would form between the prosthesis and the bone in the absence of the protein.

In a preferred embodiment of the present method a prosthetic device, such as an artificial hip replacement device, e.g., a metallic device made from titanium, for example, is first coated with an osteogenic material which induces bone ingrowth. When the device is subsequently implanted into the individual, bone growth around the site of the implant is enhanced, causing a strong bond to form between the implant and the existing bone. The present method results in enhanced biological fixation of the prosthesis in the body, which is particularly important for weight bearing prostheses. Prostheses defining a microporous surface structure are locked in place as bone formation occurs within the micropores. The metal or ceramic prosthesis may itself define such a structure, or the prosthesis may be coated to provide an adherent porous surface. Materials useful for this purpose include, for example, collagen, homopolymers of glycolic acid, lactic acid, and butyric acid, including derivatives thereof; and ceramics such as hydroxyapatite, tricalcium phosphate or other calcium phosphates. Combinations of these materials may be used. A substantially pure osteogenic protein is then bound to the uncoated or coated prosthesis. Alternatively, the osteogenic protein can be mixed with the coating material, and the mixture adhered onto the surface of the prosthesis.

In another embodiment of the present invention, osteogenic protein combined with a matrix material is packed into an orifice prepared to receive the prosthetic implant. The surface of the implant also may be coated with osteogenic protein, as described above. The implant has a shape defining one or more indentations to permit bone ingrowth. The indentations are preferably transverse to the longitudinal axis of the implant. In general, the longitudinal axis of the implant will be parallel to the longitudinal axis of the bone which has been treated to receive the implant. New bone grows into the indentations thereby filling them, integrates with the surface of the implant as described above, and integrates with existing bone. Thus, the prosthesis can be more tightly fixed into the orifice, and "latched" or held in place by bone growing into the indentations, and by osseointegration of new bone with the surface of the implant, both of which are stimulated by the osteogenic protein.

In a specific embodiment, a dental implant is used to replace missing teeth. The implant typically comprises a threaded portion which is fixed into the jawbone and a tooth portion configured to integrate with the rest of the patient's teeth. The implant is coated with osteogenic protein (with or without a matrix or carrier) and threaded or screwed into a tooth socket in the jawbone prepared to receive it (e.g., bone has been allowed to grow into and fill the socket void.) In a particularly preferred embodiment, the socket is prepared to receive the implant by packing the void with a bone growth composition composed of osteogenic protein dispersed in a suitable carrier material. The combination of osteogenic protein and carrier is referred to herein as an "osteogenic device." The osteogenic protein promotes osseointegration of the implant into the jawbone without first requiring bone growth to fill the socket, and without requiring that the prosthesis be threaded into existing bone, which may weaken the integrity of the the existing bone. Accordingly, the time interval between tooth extraction and prosthetic restoration is reduced significantly. It is anticipated that prosthetic restoration may be complete in as little time as one month. In addition, the ability of the osteogenic protein to promote osseointegration of the prosthesis will provide a superior anchor.

A prosthetic device coated with the above osteogenic protein also is the subject of the present invention. All or a portion of the device may be coated with the protein. Generally, only the portion of the device which will be in contact with the existing bone will be coated.

The present method and device results in enhanced biological fixation of the prosthesis. A strong bond is formed between the existing bone and the prosthesis, resulting in improved mechanical strength at the joining site. Higher attachment strength means that the prosthesis will be more secure and permanent, and therefore will be more comfortable and durable for the patient.

BRIEF DESCRIPTION OF THE DRAWING

The sole Figure of the drawing schematically depicts a cross-sectional view of a portion of a prosthesis implanted in a femur and illustrates the latching action of bone ingrowth in accordance with an embodiment of the invention.

DETAILED DESCRIPTION OF THE INVENTION

The present invention relates to a method for enhancing osseointegration between a prosthesis and natural bone in an individual at the site of implantation of the prosthesis. The method involves providing a prosthesis to a site of implantation together with substantially pure osteogenic protein such that the osteogenic protein is in contact with all or a portion of the implanted prosthesis. The protein promotes osseointegration of the prosthesis and the bone, resulting in a strong bond having improved tensile strength.

Osteogenic proteins which are useful in the present invention are substantially pure osteogenically active dimeric proteins. As used herein "substantially pure" means substantially free of other contaminating proteins having no endochondral bone formation activity. The protein can be either natural-sourced protein derived from mammalian bone or recombinantly produced proteins, including biosynthetic constructs. The natural-sourced proteins are characterized by having a half maximum activity of at least 25 to 50 ng per 25 mg of demineralized protein extracted bone powder, as compared to rat demineralized bone powder.

The natural-sourced osteogenic protein in its mature, native form is a glycosylated dimer having an apparent molecular weight of about 30 kDa as determined by SDS-PAGE. When reduced, the 30 kDa protein gives rise to two glycosylated peptide subunits having apparent molecular weights of about 16 kDa and 18 kDa. In the reduced state, the protein has no detectable osteogenic activity. The unglycosylated protein, which also has osteogenic activity, has an apparent molecular weight of about 27 kDa. When reduced, the 27 kDa protein gives rise to two unglycosylated polypeptides having molecular weights of about 14 kDa to 16 kDa. The recombinantly-produced osteogenic protein describes a class of dimeric proteins capable of inducing endochondral bone formation in a mammal comprising a pair of polypeptide chains, each of which has an amino acid sequence sufficiently duplicative of the sequence of the biosynthetic constructs or COP-5 Or COP-7, (SEQ. ID NOS.3 and 4), such that said pair of polypeptide chains, when disulfide bonded to produce a dimeric species is capable of inducing endochondral bone formation in a mammal. As defined herein, "sufficiently duplicative" is understood to describe the class of proteins having endochondral bone activity as dimeric proteins implanted in a mammal in association with a matrix, each of the subunits having at least 60% amino acid sequence homology in the C-terminal cysteine-rich region with the sequence of OPS (residues 335 to 431, SEQ. ID No. 1). "Homology" is defined herein as amino acid sequence identity or conservative amino acid changes within the sequence, as defined by Dayoff, et al., *Atlas of Protein Sequence and Structure;* vol.5, Supp.3, pp.345-362, (M. O. Dayoff, ed. Nat'l Biomed. Research Fdn., Washington, D.C., 1979.) Useful sequences include those comprising the C-terminal sequences of DPP (from Drosophila), Vgl (from Xenopus), Vgr-1 (from mouse), the OP1 and OP2 proteins, the CBMP2, CBMP3, and CBMP4 proteins (see U.S. Pat. No. 5,011,691 and U.S. application Ser. No. 07/841,646 by Oppermann et al., filed Feb. 21, 1992, now U.S. Pat. No. 5,266,683 the disclosures of both of which are hereby incorporated by reference, as well as the proteins referred to as BMP5 and BMP6 (see WO90/11366, PCT/US90/01630.) A number of these proteins also are described in WO88/00205, U.S. Pat. No. 5,013,649 and WO91/18098. Table I provides a list of the preferred members of this family of osteogenic proteins.

TABLE I

| | OSTEOGENIC PROTEIN SEQUENCES |
|---|---|
| hOP1 | DNA sequence encoding human OP1 protein (Seq. ID No. 1 or 3). Also referred to in related applications as "OPI", "hOP-1" and "OP-1". |
| OP1 | Refers generically to the family of osteogenically active proteins produced by expression of part or all of the hOP1 gene. Also referred to in related applications as "OPI" and OP-1". |
| hOP1-PP | Amino acid sequence of human OP1 protein (prepro form), Seq. ID No. 1, residues 1–431. Also referred to in related applications as "OP1-PP" and "OPP". |
| OP1-18Ser | Amino acid sequence of mature human OP1 protein, Seq. ID No. 1, residues 293–431. N-terminal amino acid is serine. Originally identified as migrating at 18 kDa on SDS-PAGE in COS cells. Depending on protein glycosylation pattern in different host cells, also migrates at 23kDa, 19kDa and 17kDa on SDS-PAGE. Also referred to in related applications as "OP1-18". |
| OPS | Human OP1 protein species defining the conserved 6 cysteine skeleton in the active region (97 amino acids, Seq. ID No. 1, residues 335–431). "S" stands for "short". |
| OP7 | Human OP1 protein species defining the conserved 7 cysteine skeleton in the active region (102 amino acids, Seq. ID No. 1, residues 330–431). |
| OP1-16Ser | N-terminally truncated mature human OP1 protein species. (Seq. ID No. 1, residues 300–431). N-terminal amino acid is serine; protein migrates at 16kDa or 15kDa on SDS-PAGE, depending on glycosylation pattern. Also referred to in related applications as "OP-16S". |
| OP1-16Leu | N-terminally truncated mature human OP1 protein species, Seq. ID No. 1, residues 313–431. N-terminal amino acid is leucine; protein migrates at 16 or 15kDa on SDS-PAGE, depending on glycosylation pattern. Also referred to in related applications as "OP-16L". |
| OP1-16Met | N-terminally truncated mature human OP1 protein species. Seq. ID No. 1, residues 315–431. N-terminal amino acid is methionine;. protein migrates at 16 or 15kDa on SDS-PAGE, depending on glycosylation pattern. Also referred to in related applications as "OP-16M". |
| OP1-16Ala | N-terminally truncated mature human OP1 protein species, Seq. ID No. 1 residues 316–431. N-terminal amino acid is alanine, protein migrates at 16 or 15 kDa on SDS-PAGE, depending on glycosylation pattern. Also referred to in related applications as "OP-16A". |
| OP1-16Val | N-terminally truncated mature human OP1 protein species, Seq. ID No. 1, residues 318–431. N-terminal amino acid is valine; protein migrates at 16 or 15 kDa on SDS-PAGE, depending on glycosylation pattern. Also referred to in related applications as "OP-16V". |
| mOP1 | DNA encoding mouse OP1 protein, Seq. ID No. 8. Also referred to in related applications as "mOP-1". |
| mOP1-PP | Prepro form of mouse protein, Seq. ID No. 8, residues 1–430. Also referred to in related applications as "mOP-1-PP". |
| mOP1-Ser | Mature mouse OP1 protein species (Seq. ID No. 8, residues 292–430). N-terminal amino acid is serine. Also referred to in related applications as "mOP1" and "mOP-1". |

TABLE I-continued
OSTEOGENIC PROTEIN SEQUENCES

| | |
|---|---|
| mOP2 | DNA encoding mouse OP2 protein, Seq. ID No. 12. Also referred to in related applications as "mOP-2". |
| mOP2-PP | Prepro form of mOP2 protein, Seq. ID No. 12, residues 1–399. Also referred to in related applications as "mOP-2-PP". |
| mOP2-Ala | Mature mouse OP2 protein, Seq ID No. 12, residues 261–399. N-terminal amino acid in alanine. Also referred to in related applications as "mOP2" and "mOP-2". |
| hOP2 | DNA encoding human OP2 protein, Seq. ID No. 10. Also referred to in related applications as "hOP-2". |
| hOP2-PP | Prepro form of human OP2 protein, Seq. ID No. 10, res. 1–402). Also referred to in related applications as "hOP-2-PP". |
| hOP2-Ala | Possible mature human OP2 protein species: Seq. ID No. 10, residues 264–402. Also referred to in related applications as "hOP-2". |
| hOP2-Pro | Possible mature human OP2 protein species: Seq. ID No. 10, residues 267–402. N-terminal amino acid is proline. Also referred to in related applications as "hOP-2P". |
| hOP2-Arg | Possible mature human OP2 protein species: Seq. ID No. 10, res. 270–402. N-terminal amino acid is arginine. Also referred to in related applications as "hOP-2R". |
| hOP2-Ser - | Possible mature human OP2 protein species: Seq. ID No. 10, res. 243–402. N-terminal amino acid is serine. Also referred to in related applications as "hOP-2S". |
| Vgr-1-fx | C-terminal 102 amino acid residues of the murine "Vgr-1" protein (Seq. ID No. 7). |
| CBMP2A | C-terminal 101 amino acid residues of the human BMP2A protein. (Residues 296–396 of Seq. ID No. 14). |
| CBMP2B | C-terminal 101 amino acid residues of the human BMP2B protein. (Seq. ID No. 18). |
| BMP3 | Mature human BMP3 (partial sequence, Seq. ID No. 16. See U.S. Pat. No. 5,011,691 for C-terminal 102 residues, "CBMP3.") |
| BMP5-fx | C-terminal 102 amino acid residues of the human BMP5 protein. (Seq ID No. 20). |
| BMP6-fx | C-terminal 102 amino acid residues of the human BMP6 protein. (Seq ID No. 21). |
| COP5 | Biosynthetic ostegenic 96 amino acid sequence (Seq. ID No. 3). |
| COP7 | Biosynthetic ostegenic 96 amino acid sequence (Seq. ID No. 4). |
| DPP—fx | C-terminal 102 amino acid residues of the Drosophila "DPP" protein (Seq. ID No. 5). |
| Vgl-fx | C-terminal 102 amino acid residues of the Xenopus "Vgl" protein (Seq. ID No. 6). |

The members of this family of proteins share a conserved six or seven cysteine skeleton in this region (e.g., the linear arrangement of these C-terminal cysteine residues is conserved in the different proteins.) See, for example, OPS, whose sequence defines the six cysteine skeleton, or OP7, a longer form of OP1, comprising 102 amino acids and whose sequence defines the seven cysteine skeleton.) In addition, the OP2 proteins contain an additional cysteine residue within this region.

This family of proteins includes longer forms of a given protein, as well as species and allelic variants and biosynthetic mutants, including addition and deletion mutants and variants, such as those which may alter the conserved C-terminal cysteine skeleton, provided that the alteration still allows the protein to form a dimeric species having a conformation capable of inducing bone formation in a mammal when implanted in the mammal in association with a matrix. In addition, the osteogenic proteins useful in devices of this invention may include forms having varying glycosylation patterns and varying N-termini, may be naturally occurring or biosynthetically derived, and may be produced by expression of recombinant DNA in procaryotic or eucaryotic host cells. The proteins are active as a single species (e.g., as homodimers), or combined as a mixed species.

A particularly preferred embodiment of the proteins useful in the prosthetic devices of this invention includes proteins whose amino acid sequence in the cysteine-rich C-terminal domain has greater than 60% identity, and preferably greater than 65% identity with the amino acid sequence of OPS.

In another preferred aspect, the invention comprises osteogenic proteins comprising species of polypeptide chains having the generic amino acid sequence herein referred to as "OPX" which accommodates the homologies between the various identified species of the osteogenic OP1 and OP2 proteins, and which is described by the amino acid sequence of Sequence ID No. 22.

In still another preferred aspect, the invention comprises nucleic acids and the osteogenically active polypeptide chains encoded by these nucleic acids which hybridize to DNA or RNA sequences encoding the active region of OP1 or OP2 under stringent hybridization conditions. As used herein, stringent hybridization conditions are defined as hybridization in 40% formamide, 5×SSPE, 5×Denhardt's Solution, and 0.1% SDS at 37° C. overnight, and washing in 0.1×SSPE, 0.1% SDS at 50° C.

The invention further comprises nucleic acids and the osteogenically active polypeptide chains encoded by these nucleic acids which hybridize to the "pro" region of the OP1 or OP2 proteins under stringent hybridization conditions. As used herein, "osteogenically active polypeptide chains" is understood to mean those polypeptide chains which, when dimerized, produce a protein species having a conformation such that the pair of polypeptide chains is capable of inducing endochondral bone formation in a mammal when implanted in a mammal in association with a matrix or carrier.

Given the foregoing amino acid and DNA sequence information, the level of skill in the art, and the disclosures of U.S. Pat. No. 5,011,691 and published PCT specification U.S. Ser. No. 89/01469, published Oct. 19, 1989, the disclosures of which are incorporated herein by reference, various DNAs can be constructed which encode at least the active domain of an osteogenic protein useful in the devices of this invention, and various analogs thereof (including species and allelic variants and those containing genetically engineered mutations), as well as fusion proteins, truncated forms of the mature proteins, deletion and addition mutants, and similar constructs. Moreover, DNA hybridization probes can be constructed from fragments of any of these proteins, or designed de novo from the generic sequence. These probes then can be used to screen different genomic and cDNA libraries to identify additional osteogenic proteins useful in the prosthetic devices of this invention.

The DNAs can be produced by those skilled in the art using well known DNA manipulation techniques involving genomic and cDNA isolation, construction of synthetic DNA from synthesized oligonucleotides, and cassette mutagenesis techniques. 15–100 mer oligonucleotides may be synthesized on a DNA synthesizer, and purified by polyacrylamide gel electrophoresis (PAGE) in Tris-Borate-EDTA buffer. The DNA then may be electroeluted from the gel. Overlapping oligomers may be phosphorylated by T4 polynucleotide kinase and ligated into larger blocks which may also be purified by PAGE.

The DNA from appropriately identified clones then can be isolated, subcloned (preferably into an expression vector), and sequenced. Plasmids containing sequences of interest then can be transfected into an appropriate host cell for protein expression and further characterization. The host may be a procaryotic or eucaryotic cell since the former's inability to glycosylate protein will not destroy the protein's morphogenic activity. Useful host cells include *E. coli*, Saccharomyces, the insect/baculovirus cell system, myeloma cells, CHO cells and various other mammalian cells. The vectors additionally may encode various sequences to promote correct expression of the recombinant protein, including transcription promoter and termination sequences, enhancer sequences, preferred ribosome binding site sequences, preferred mRNA leader sequences, preferred signal sequences for protein secretion, and the like.

The DNA sequence encoding the gene of interest also may be manipulated to remove potentially inhibiting sequences or to minimize unwanted secondary structure formation. The recombinant osteogenic protein also may be expressed as a fusion protein. After being translated, the protein may be purified from the cells themselves or recovered from the culture medium. All biologically active protein forms comprise dimeric species joined by disulfide bonds or otherwise associated, produced by folding and oxidizing one or more of the various recombinant polypeptide chains within an appropriate eucaryotic cell or in vitro after expression of individual subunits. A detailed description of osteogenic proteins expressed from recombinant DNA in *E. coli* is disclosed in U.S. Ser. No. 422,699 filed Oct. 17, 1989, the disclosure of which is incorporated herein by reference. A detailed description of osteogenic proteins expressed from recombinant DNA in numerous different mammalian cells is disclosed in U.S. Ser. No. 569,920 filed Aug. 20, 1990, the disclosure of which is hereby incorporated by reference.

Alternatively, osteogenic polypeptide chains can be synthesized chemically using conventional peptide synthesis techniques well known to those having ordinary skill in the art. For example, the proteins may be synthesized intact or in parts on a solid phase peptide synthesizer, using standard operating procedures. Completed chains then are deprotected and purified by HPLC (high pressure liquid chromatography). If the protein is synthesized in parts, the parts may be peptide bonded using standard methodologies to form the intact protein. In general, the manner in which the osteogenic proteins are made can be conventional and does not form a part of this invention.

The osteogenic proteins useful in the present invention are proteins which, when implanted in a mammalian body, induce the developmental cascade of endochondral bone formation including recruitment and proliferation of mesenchymal cells, differentiation of progenitor cells, cartilage formation, calcification of cartilage, vascular invasion, bone formation, remodeling and bone marrow differentiation. The osteopenic protein in contact with the present prostheses can induce the full developmental cascade of endochondral bone formation at the site of implantation essentially as it occurs in natural bone healing.

Prostheses which can be used with the present method include porous or non-porous orthopedic prostheses of the types well known in the art. Such prostheses are generally fabricated from rigid materials such as metals, including for example, stainless steel, titanium, molybdenum, cobalt, chromium and/or alloys or oxides of these metals. Such oxides typically comprise a thin, stable, adherent metal oxide surface coating. The prostheses are preferably formed from or coated with porous metals to permit infiltration of the bone, but non-porous materials also can be used. Porous metallic materials for use in prostheses are described, for example, by Spector in *J. Arthroplasty*, 2(2):163-176 (1987), and by Cook et al. in *Clin. Orthoped. and Rel. Res.*, 232:225-243 (1988), the teachings of both of which are hereby incorporated herein by reference. Metallic prostheses may be used for major bone or joint replacement and for repairing non-union fractures, for example, where the existing bone has been destroyed by disease or injury.

In a preferred embodiment of the present device and method, the prosthesis is coated with a material which enhances bone ingrowth and fixation, in addition to the protein. Materials which are useful for this purpose are biocompatible, and preferably in vivo biodegradable and nonimmunogenic. Such materials include, for example, collagen, hydroxyapatite, homopolymers or copolymers of glycolic acid lactic acid, and butyric acid and derivatives thereof, tricalcium phosphate or other calcium phosphates, metal oxides, (e.g., titanium oxide), and demineralized, guanidine extracted bone.

The present coated prostheses are prepared by applying a solution of the protein, and optionally, hydroxylapatite or other material to all or a portion of the prosthesis. The protein can be applied by any convenient method, for example, by dipping, brushing, immersing, spraying or freeze-drying. Hydroxylapatite is preferably applied by a plasma spraying process. The protein is preferably applied by immersing the prostheses in a solution of the protein under conditions appropriate to induce binding or precipitation of the protein from solution onto the implant. The amount of protein which is applied to the implant should be a concentration sufficient to induce endochondral bone formation when the prosthesis is implanted in the recipient. Generally a concentration in the range of at least 5 $\mu$g protein per 3.4 cm$^2$ surface area is sufficient for this purpose. If hydroxylapatite or other carrier material is used, it is applied to the prosthesis in an amount required to form a coating of from about 15$\mu$ to about 60$\mu$ thick. A layer about 25$\mu$ thick of hydroxylapatite has been used to improve implant fixation, as shown in the exemplification.

In one aspect, the prosthesis comprises a device configured for insertion into an orifice prepared to receive the prosthesis. In this embodiment, as illustrated in the Figure, the interior of a bone 10 is hollowed out in preparation for insertion of the implant 12. The implant has a contoured surface design 14 defining plural indentations 16 to permit ingrowth of bone into the indentations. The indentations are preferably transverse to the longitudinal axis 18 of the implant. The contoured portion to be inserted in the orifice may be coated with osteogenic protein as described above. Osteogenic protein combined with a matrix material 20 is packed into the orifice with the prosthetic implant, thereby surrounding it. Stimulated by the osteogenic protein, new bone grows into the indentations 16 and becomes integrated with the surface of the implant 12 and with pre-existing bone 10 as described above. Thus, the prosthesis is both mechanically and biologically fixed in place, and axial movement of the implant relative to the bone requires shearing of bone tissue. Matrix material 20 can be any of the materials described above for coating the prosthesis for enhancing bone growth and fixation, e.g., collagen, hydroxyapatite, homopolymers or copolymers of glycolic acid lactic acid, and butyric acid and derivatives thereof, tricalcium phosphate or other calcium phosphates, metal oxides and demineralized, guanidine extracted bone. Matrix materials for use with osteogenic proteins which can be used in the present embodiment are those described, for example, in U.S. Pat. No. 5,011,691 and in copending U.S. patent application Ser. No. 07/841,646 by Oppermann et al., filed Feb. 21, 1992, now U.S. Pat. No. 5,226,683, the teachings of which are hereby incorporated by reference.

The prothesis illustrated in the Figure is particularly useful for dental and other implants where at last part of the prosthesis is to be embedded into bone tissue. Packing the orifice, e.g., tooth socket, with an "osteogenic device," e.g., osteogenic protein in combination with a matrix material, provides a solid material in which to embed the prosthesis without requiring that the device be threaded into existing bone. Moreover, the osteogenic protein stimulates endochondral bone formation within the socket and into and around the implant, thereby obviating the previously required step of first allowing bone ingrowth into the socket in order to provide a suitable surface into which to implant the prosthesis. Accordingly, using the method and devices of the invention, strong fixation of an implanted prosthesis may be achieved in a fraction of the time previously required, significantly shortening the time interval between tooth extraction and prosthetic restoration. In addition, this treatment may expand the use of implant therapy and enhance success rates by eliminating a surgical procedure, reducing the amount of bone lost following tooth extraction, permitting the insertion of longer implants and minimizing prosthetic compromises necessitated by alveolar ridge resorption.

The invention will be further illustrated by the following Exemplification which is not intended to be limiting in any way.

EXEMPLIFICATION

Example 1

Metal Implant Fixation

Cylindrical implants 18 mm in length and 5.95±0.05 mm in diameter were fabricated from spherical Co-Cr-Mo particles resulting in a pore size of 250–300 μm and a volume porosity of 38–40%. A highly crystalline, high density and low porosity hydroxylapatite (HA) coating was applied by plasma spray process to one-half of the length of each of the implants. The coating thickness was 25 μm and did not alter the porous coating morphology.

In the initial study, three implants were treated with a partially purified bovine OP (bOP) preparation. The bOP was naturally sourced OP extracted from cortical bone and partially purified through the Sephacryl-300 HR step in the purification protocol as described in Sampath et al. (1990), *J. Biol. Chem.*, 265: 13198–13205. 200 μl aliquots of 4M guanidine-HCl, 50 mM Tris-HCl, pH 7.0, containing approximately 80 μg bOP were added to each implant in an eppendorf tube. After overnight incubation at 4° C. the protein was precipitated and the implant washed with 80% ethanol. The implants were subsequently freeze dried. Two implants without bOP served as the controls.

The implants were evaluated in one skeletally mature adult mongrel dog (3–5 years old, 20–25 Kg weight) using the femoral transcortical model. Standard surgical techniques were used such that the animal received the five implants in one femur. At three weeks the dog was sacrificed and the femur removed.

The harvested femur was sectioned transverse to the long axis such that each implant was isolated. Each implant was sectioned in half to yield one HA-coated and one uncoated push-out sample. Interface attachment strength was determined using a specifically designed test fixture. The implants were pushed to failure with a MTS test machine at a displacement rate of 1.27 mm/minute. After testing, all samples were prepared for standard undecalcified histologic and microradiographic analyses. The sections (4 sections from each implant) were qualitatively examined for the type and quality of tissue ingrowth, and quantitatively evaluated for % bone ingrowth with a computerized image analysis system. The mechanical and quantitative histological data is shown in Table II.

TABLE II

| METAL IMPLANTS - bOP | | |
|---|---|---|
| | 3 WEEKS | |
| | HA-Coated | Uncoated |
| Interface Shear Strength, MPa | | |
| Control | 9.70 | 3.40 |
| | (n = 2) | (n = 2) |
| Protein (bOP) | 10.75 | 4.08 |
| | (n = 3) | (n = 3) |
| Percent Bone Ingrowth | | |
| Control | 42.56 | 37.82 |
| | (n = 4) | (n = 4) |
| Protein (bOP) | 51.66 | 46.38 |
| | (n = 4) | (n = 4) |

Both the mechanical and histological data suggested that bOP enhanced osseointegration of the implants. Both the HA-coated and uncoated implants showed an increase of shear strength and bone ingrowth compared with untreated controls. Moreover, the HA-coated implants appeared to show significant enhancement compared to the uncoated implant. The histological sections directly showed a greater number of cells between the metal pores.

The positive results of the initial implant study prompted a more detailed study. Twenty-seven implants were treated with a recombinant human OP1 protein. The OP1 protein was produced by transformed CHO cells. Details for the recombinant production of OP1 are disclosed in U.S. Ser. No. 841,646, incorporated hereinabove by reference. The protein was purified to contain as the major species the protein designated OP1-18Ser (Seq. ID No. 1, residues 293–431), and about 30% truncated forms of OP1 (e.g., OP1-16 Ser, OP1-16 Leu, OP1-16 Met, OP1-16 Ala and OP1-16 Val). The protein was greater than 90% pure. The implants were immersed for 30 minutes in 200 μl 50% ethanol/0.01% TFA containing 5 μg recombinant protein and the solution frozen in an ethanol/dry ice bath while the formulation tube was rolled. The tubes were subsequently freeze dried. Nineteen implants were also prepared by treatment with ethanol/TFA without the OP1 protein by the same procedure.

In test implants, it was found that OP1 could be extracted from treated implants with 8M urea, 1% Tween 80, 50 mM Tris, pH 8.0 and analyzed by HPLC. By this method, it was shown that all of the OP1 in the formulation tubes bound to the implant under the conditions employed. Furthermore, since the test implants were half coated with HA, additional implants were obtained to independently evaluate the binding of OP1 to each of these surfaces. Initial binding studies showed that the OP1 binds more readily to the HA than to the uncoated metal.

The implants for the second study were evaluated in skeletally mature adult mongrel dogs using the femoral transcortical model. Standard aseptic surgical techniques were used such that each animal received five implants bilaterally. Implantation periods of three weeks were used. The mechanical and quantitative histological data are shown in Table III. Three HA-coated and uncoated configurations were evaluated: controls (no treatment), precoat samples (formulated without OP1) and the OP1 samples.

TABLE III

METAL IMPLANTS - OP-1

| | INTERFACE SHEAR ATTACHMENT STRENGTH, MPA 3 Weeks: | | PERCENT BONE INGROWTH 3 Weeks: | |
|---|---|---|---|---|
| | HA-coated | Uncoated | HA-coated | Uncoated |
| Control | 7.59 ± 2.99 (n = 10) | 6.47 ± 1.23 (n = 10) | 44.98 ± 12.57 (n = 24) | 41.66 ± 11.91 (n = 24) |
| Precoat | 7.85 ± 3.43 (n = 9) | 6.49 ± 2.20 (n = 9) | 40.73 ± 16.88 (n= 24) | 39.14 ± 16.18 (n = 24) |
| Protein (hOP-1) | 8.69 ± 3.17 (n = 17) | 6.34 ± 3.04 (n = 17) | 48.68 ± 16.61 (n = 24) | 47.89 ± 11.91 (n = 24) |

Mechanical testing results demonstrated enhanced attachment strength for the HA-coated samples as compared to the uncoated samples. At three weeks the greatest fixation was observed with the HA-coated implant with protein.

Histologic analysis demonstrated greater bone ingrowth for all HA-coated versus uncoated samples although the differences were not significant. The percent bone ingrowth was greatest for the HA-coated and uncoated implants with the protein present. Linear regression analysis demonstrated that attachment strength was predicted by amount of bone growth into the porous structure, presence of HA coating, and presence of protein.

Example 2

Titanium frequently is used to fabricate metal prostheses. The surface of these prostheses comprise a layer of titanium oxide. Therefore, titanium oxide itself was evaluated for its ability to serve as a carrier for OP-1 and in general for its biocompatibility with the bone formation process. The in vivo biological activity of implants containing a combination of titanium oxide and OP-1 (Sequence ID No. 1, residues 293-431) was examined in rat subcutaneous and intramuscular assays. Implants contained 0, 6.25, 12.5, 25 or 50 μg of OP-1 formulated onto 30 mg of titanium oxide.

Implants were formulated by a modification of the ethanol/TFA freeze-drying method. Titanium oxide pellets were milled and sieved to a particle size of 250-420 microns. 30 mg of these particles were mixed with 50 μl aliquots of 45% ethanol, 0.09% trifluoroacetic acid containing no OP-1 or various concentrations of OP-1. After 3 hours at 4° C., the samples were frozen, freeze-dried and implanted into rats.

After 12 days in vivo the implants were removed and evaluated for bone formation by alkaline phosphatase specific activity, calcium content and histological evidence. The results showed that OP-1 induced the formation of bone at each concentration of OP-1 at both the subcutaneous and intramuscular implant sites. No bone formed without OP-1 added to the titanium oxide. The amount of bone as quantitated by calcium content of the implants was similar to that observed using bone collagen carriers. Therefore titanium is a useful carrier for osteogenic proteins and is biocompatible with the bone formation process.

Example 3

The efficacy of the method of this invention on standard dental prosthesis may be assessed using the following model and protocol. Maxillary and mandibular incisor and mandibular canine teeth are extracted from several (e.g., 3) male cynomolgus (Macca fascularis) monkeys (4-6 kilograms) under ketamine anesthesia and local infiltration of lidocaine. Hemostasis is achieved with pressure.

The resultant toothless sockets are filled either with (a) collagen matrix (CM), (b) with collagen matrix containing osteogenic protein, such as the recombinantly produced OP1 protein used in Example 1, above (e.g., an ostegenic device) or c) are left untreated. Titanium, self-tapping, oral, endosseous implants (Nobelpharma, Chicago, Ill.) are inserted into all of the sockets by minimally engaging the self-tapping tip. The mucoperiosteal flap is released from the underlying tissue and used to obtain primary wound closure using standard surgical procedures known in the medical art.

The animals are sacrificed after three weeks by lethal injection of pentobarbital and perfusion with paraformaldehyde-glutaraldehyde. The jaws then are dissected and the blocks containing the appropriate sockets are resected, further fixed in neutral buffered formalin, decalcified in formic acid and sodium citrate, embedded in plastic and stained with basic Fuchsin and toluidine blue. Sections then are analyzed by light microscopy. Preferably, computer assisted histomorphometric analysis is used to evaluate the new tissue, e.g., using Image 1.27 and Quick Capture$^R$ (Data Translation, Inc. Marlboro, Mass. 07152).

It is anticipated that sockets which contain the osteogenic device will induce the formation of new bone in close apposition to the threaded surface of the titanium implants within 3 weeks. By contrast, sockets treated only with collagen matrix or sockets receiving neither collagen matrix nor the osteogenic device should show no evidence of new bone formation in close apposition to the implant surface.

Equivalents

One skilled in the art will be able to ascertain, using no more than routine experimentation, many equivalents to the subject matter described herein. Such equivalents are intended to be encompassed by the following claims.

What is claimed is:

1. A method for promoting in vivo osseointegration of an implantable, prosthetic device, the method comprising the steps of:
    providing on a surface of the prosthetic device substantially pure osteogenic protein, and
    implanting the device in a mammal at a site wherein bone tissue and said surface are maintained at least partially in contact for a time sufficient to permit enhanced bone tissue growth between said tissue and said device; wherein said osteogenic protein is a basic protein comprising a pair of polypeptide chains, one of said polypeptide chains comprising an amino acid sequence sharing greater than 60% identity with the amino acid sequence defined by residues 335 to 431 of Seq. ID No. 1 (OPS) such that said pair of polypeptide chains, when disulfide bonded to produce a dimeric species, has a conformation capable of inducing endochondral bone formation when disposed in a matrix and implanted in a mammal.

2. In the method of repairing the skeletal system of a mammal comprising surgically implanting in contact with bone tissue a prosthetic device, and permitting the device and the bone tissue to integrate to form a weight bearing skeletal component, the improvement comprising:
    providing substantially pure osteogenic protein on a surface of said device prior to its implantation thereby to promote enhanced bone tissue growth into said device and to improve the tensile strength of the junction between the bone and said device; wherein said protein is an osteogenically active protein, characterized in that the protein is a basic protein comprising a pair of polypeptide chains, one of said polypeptide chains comprising an amino acid sequence sharing greater than 60% identity with the amino acid sequence defined by residues 335 to 431 of Seq. ID No. 1 (OPS) such that said pair of polypeptide chains, when disulfide bonded to produce a dimeric species, has a conformation capable of inducing endochondral bone formation when disposed in a matrix and implanted in a mammal.

3. The method of claim 1 or 2 wherein said surface of said prosthetic device further comprises hydroxylapatite, collagen, homopolymers or copolymers of glycolic acid, lactic acid or butyric acid and derivatives thereof, tricalcium phosphate or other calcium phosphate, metal oxides or combinations thereof.

4. The method of claims 1 or 2 wherein the prosthetic device comprises a porous, metallic material.

5. The method of claim 1 or 2 wherein said dimeric osteogenic protein is produced by recombinant DNA in a host cell and is isolated therefrom.

6. The method of claim 1 or 2 wherein the osteogenic protein is an osteogenically active dimeric protein expressed from recombinant DNA in a host cell, further characterized in that the protein comprises a pair of oxidized subunits disulfide bonded to produce a dimeric species, one of said subunits having an amino acid sequence encoded by a nucleic acid capable of hybridizing to a nucleic acid encoding OPS (residues 335 to 431 of Seq. ID No. 1) under stringent hybridization conditions, such that the disulfide bonded dimeric species comprising said subunit has a conformation capable of inducing endochondral bone formation in a mammal when disposed on the surface of said device.

7. The method of claim 5 wherein said dimeric osteogenic protein is unglycosylated.

8. The method of claim 1 or 2 wherein each said polypeptide chain of said protein comprises an amino acid sequence sharing greater than 65% identity with an amino acid sequence comprising OPS.

9. The method of claim 8 wherein the amino acid sequence of one of said polypeptide chains comprises the amino acid sequence defined by residues 335–431 of Seq. ID No. 1 (OPS).

10. The method of claim 8 wherein both said polypeptide chains comprise the amino acid sequence defined by residues 335–431 of Seq. ID No. 1 (OPS.)

11. The method of claim 10 wherein both said polypeptide chains comprise the amino acid sequence of residues 318–431 of Seq. ID No. 1 (OP1-16 Val.)

12. An improved prosthetic device for repairing mammalian skeletal defects, injuries, or anomalies comprising a rigid prosthetic implant having a porous or non-porous surface region for implantation adjacent bone tissue, wherein the improvement comprises:
substantially pure osteogenically active osteogenic protein disposed on said surface region in an amount sufficient to promote enhanced bone tissue growth into said surface; wherein said protein is an osteogenically active protein, characterized in that the protein is a basic protein comprising a pair of polypeptide chains, one of said polypeptide chains comprising an amino acid sequence sharing greater than 60% identity with the amino acid sequence defined by residues 335 to 431 of Seq. ID No. 1 (OPS) such that said pair of polypeptide chains, when disulfide bonded to produce a dimeric species, has a conformation capable of inducing endochondral bone formation when disposed in a matrix and implanted in a mammal.

13. The device of claim 12 wherein said surface of said prosthetic device further comprises hydroxylapatite.

14. The device of claim 12 wherein said dimeric osteogenic protein is produced by recombinant DNA in a host cell and is isolated therefrom.

15. The device of claim 14 wherein said dimeric osteogenic protein is unglycosylated.

16. The device of claim 12 wherein one of said polypeptide chains comprises an amino acid sequence encoded by a nucleic acid capable of hybridizing to a nucleic acid encoding OPS (residues 335–431 of Seq. ID No. 1), such that the disulfide bonded dimeric species comprising said polypeptide chain has a conformation capable of inducing endochondral bone formation in a mammal when disposed on the surface of said device.

17. The device of claim 12 wherein each of said polypeptide chains comprises an amino acid sequence sharing greater than 65% identity with the amino acid sequence defined by residues 335 to 431 of Seq. ID No. 1 (OPS).

18. The device of claim 17 wherein one of said polypeptide chains of said protein comprises residues 335–431 of Seq. ID No. 1 (OPS).

19. The device of claim 17 wherein both said polypeptide chains comprise the amino acid sequence defined by residues 335–431 of Seq. ID No. 1 (OPS).

20. The device of claim 19 wherein both said polypeptide chains comprise the amino acid sequence defined by residues 318–431 of Seq. ID No. 1 (OP1-16 Val.)

21. The device of claim 12 wherein the prosthesis comprises a porous metallic material.

22. The device of claim 12 wherein the prosthesis comprises a contoured implantable portion for insertion into an orifice having plural indentations transverse to its longitudinal axis.

23. The device of claim 22 comprising a dental implant.

24. A method for promoting in vivo osseointegration of a prosthetic device into an orifice of a bone, comprising the steps of:
providing a prosthetic device having a contoured implantable portion for insertion into said orifice, said contoured portion having plural indentations transverse to its longitudinal axis, and
implanting into the orifice the contoured portion of the prosthetic device and a bond growth composition comprising a substantially pure osteogenic protein combined with a matrix material which induces bone growth in said indentations, osseointegration between the bone and the prosthetic device, and osseointegration of new bone induced by said composition and said bone; wherein said protein is an osteogenically active protein, characterized in that the protein is a basic protein comprising a pair of polypeptide chains, one of said polypeptide chains comprising an amino acid sequence sharing greater than 60% identity with the amino acid sequence defined by residues 335 to 431 of Seq. ID No. 1 (OPS) such that said pair of polypeptide chains, when disulfide bonded to produce a dimeric species, has a conformation capable of inducing endochondral bone formation when disposed in a matrix and implanted in a mammal.

25. The method of claim 24 wherein the contoured portion comprises a porous metallic material.

26. The method of claim 25 wherein the osteogenic protein enhances bone ingrowth into said pores.

27. The device of claim 24 or 29 wherein said protein is produced by recombinant DNA in a host and is isolated therefrom.

28. The device of claim 27 wherein said protein is unglycosylated.

29. A device for promoting in vivo osseointegration of a prosthesis into an orifice of a bone, comprising
a rigid prosthetic implant having a contoured portion for insertion into said orifice, said contoured portion having plural indentations transverse to its longitudinal axis, and
a bone growth composition comprising a substantially pure osteogenic protein combined with a matrix material which induces bone growth in said indentations, osseointegration between the bone and the prosthetic implant and osseointegration of new bone induced by said composition and said bone; wherein said protein is an osteogenically active protein characterized in that the protein is a basic, dimeric protein and comprises a pair of polypeptide chains, one of said polypeptide chains having an amino acid sequence sharing greater than 60% identity with the amino acid sequence defined by residues 335 to 431 of Seq. ID No. 1 (OPS) such that said pair of polypeptide chains, when disulfide bonded to produce a dimeric species, has a conformation capable of inducing endochondral bone formation in association with said contoured portion of said prosthesis when implanted in a mammal.

30. The device of claim 29 wherein the contoured portion comprises a porous metallic material.

31. The device of claim 30 wherein the osteogenic protein enhances bone ingrowth into said pores.

32. The device of claim 29 wherein said matrix material is selected from the group consisting of hydroxylapatite, collagen, polymers or copolymers of glycolic acid, lactic acid or butyric acid, tricalcium phosphate or other calcium phosphates, metal oxides, demineralized guanidine extracted bone and combinations thereof.

33. The device of claim 29 comprising a dental implant.

* * * * *

UNITED STATES PATENT AND TRADEMARK OFFICE
CERTIFICATE OF CORRECTION

PATENT NO. : 5,344,654
DATED : Sep. 6, 1994
INVENTOR(S) : David C. Rueger, Thangavel Kuberasampath, Hermann Oppermann and Engin Ozkaynak It is certified that error appears in the above-indentified patent and that said Letters Patent is hereby corrected as shown below:

Title page, under Item 60 "Related U.S. Application Data," line 25, "422,613" should read —422,699—.

Title page, under Item 60 "Related U.S. Application Data", last line, after "599,543" add —is a continuation-in-part of Ser. No. 569,920, Aug. 20, 1990, said Ser. No. 616,374 is a division of Ser. No. 422,613, Oct. 17, 1989, Pat. No. 4,975,526 and 483,913, Feb. 22, 1990, Pat. No. 5,171,574.—

Claim 24, col. 62, line 48, change "bond" to —bone—.

Signed and Sealed this

Sixth Day of June, 1995

*Attest:*

BRUCE LEHMAN

*Attesting Officer*      *Commissioner of Patents and Trademarks*